(12) United States Patent
Bullington et al.

(10) Patent No.: US 10,194,853 B2
(45) Date of Patent: Feb. 5, 2019

(54) DEVICES AND METHODS FOR VERIFYING A SAMPLE VOLUME

(71) Applicant: Magnolia Medical Technologies, Inc., Seattle, WA (US)

(72) Inventors: Gregory J. Bullington, Bellevue, WA (US); Shan E. Gaw, Seattle, WA (US); Jay M. Miazga, Seattle, WA (US); Shannon E. Eubanks, Woodinville, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 101 days.

(21) Appl. No.: 15/146,967

(22) Filed: May 5, 2016

(65) Prior Publication Data

US 2016/0324454 A1 Nov. 10, 2016

Related U.S. Application Data

(60) Provisional application No. 62/157,145, filed on May 5, 2015.

(51) Int. Cl.
*B01L 3/00* (2006.01)
*A61B 5/157* (2006.01)
(Continued)

(52) U.S. Cl.
CPC ........ *A61B 5/157* (2013.01); *A61B 5/150755* (2013.01); *A61B 10/0045* (2013.01)

(58) Field of Classification Search
CPC .............. A61B 5/157; A61B 5/150755; A61B 10/0045
See application file for complete search history.

(56) References Cited

U.S. PATENT DOCUMENTS

| 5,809,674 A | 9/1998 | Key |
| 9,003,879 B1 | 4/2015 | Honan et al. |

(Continued)

FOREIGN PATENT DOCUMENTS

| WO | WO 2008/031036 A1 | 3/2008 |
| WO | WO 2016/179347 | 10/2016 |

OTHER PUBLICATIONS

International Search Report and Written Opinion for International Application No. PCT/US2016/030888, dated Aug. 12, 2016, 12 pages.

(Continued)

*Primary Examiner* — Dennis White
(74) *Attorney, Agent, or Firm* — Cooley LLP

(57) ABSTRACT

A system for verifying a sample volume includes a sample reservoir and a volumetric verification device. The sample reservoir defines an inner volume and is configured to receive a volume of bodily fluid. The inner volume of the sample reservoir contains an additive. The volumetric verification device includes a first indicator and a second indicator. The volumetric verification device is configured to selectively engage the sample reservoir to (1) place the first indicator in a first position along a length of the sample reservoir such that the first indicator is substantially aligned with a surface and/or meniscus of the additive and (2) place the second indicator in a second position along the length of the sample reservoir such that the second indicator is substantially aligned with a predetermined fill volume when bodily fluid is transferred to the inner volume.

20 Claims, 9 Drawing Sheets

(51) Int. Cl.
    *A61B 5/15* (2006.01)
    *A61B 10/00* (2006.01)

(56) References Cited

U.S. PATENT DOCUMENTS

| | | |
|---|---|---|
| 2004/0147878 A1 | 7/2004 | Lyon et al. |
| 2011/0042255 A1 | 2/2011 | Traboulsi et al. |
| 2014/0193848 A1 | 7/2014 | Kaufman |
| 2015/0094615 A1 | 4/2015 | Patton |

OTHER PUBLICATIONS

Patel, R. et al., "Optimized Pathogen Detection with 30- Compared to 20-Milliliter Blood Culture Draws." Journal of Clinical Microbiology, 49(12):4047-4051 (2011).
Extended European Search Report dated Sep. 3, 2018 for European Application No. 16790058.8, 9 pages.

DEVICES AND METHODS FOR VERIFYING A SAMPLE VOLUME

CROSS-REFERENCE TO RELATED APPLICATIONS

This application claims priority to and the benefit of U.S. Provisional Patent Application Ser. No. 62/157,145 entitled, "Devices and Methods for Verifying a Sample Volume," filed May 5, 2015, the disclosure of which is incorporated herein by reference in its entirety.

BACKGROUND

Embodiments described herein relate generally to the parenteral procurement of bodily fluid samples, and more particularly to devices and methods for parenterally procuring bodily fluid samples with reduced contamination from microbes and for verifying the bodily fluid sample volumes.

The in vitro diagnostics industry has expanded the types of approaches employed to identify, categorize, type, determine sensitivity and susceptibility (e.g., to specific antibiotics), and/or to otherwise discern desired information about bodily fluid samples with increased speed, specificity, and accuracy. For example, some such approaches include DNA/RNA sequencing, biological marker identification, mass spectrometry, centrifuging, magnetic separation, microfluidic isolation, molecular analysis, polymerase chain reaction (PCR) analysis, whole blood analysis, and/or the like. In some instances, such approaches can be used, for example, in microbial testing of parenterally obtained bodily fluids to determine the presence of one or more potentially undesirable microbes, such as bacteria, fungi, or yeast (e.g., *Candida*).

In some instances, microbial testing may include diagnostic methods including but not limited to incubating patient samples in one or more sterile vessels containing culture media that is conducive to microbial growth, molecular sample analysis, gene sequencing, PCR-based approaches, mass spectrometry, and/or the like, as noted above. Generally, when such microbes are present in the patient sample, the microbes flourish over time in the culture medium or can be detected and/or identified by one of the aforementioned technological approaches. When culture medium is utilized for microbial testing, after a variable amount of time (e.g., a few hours to several days), organism growth can be detected by automated, continuous monitoring (e.g., by detecting carbon dioxide and/or the like). The culture medium can then be tested for the presence of the microbes, which if present, suggests the presence of the same microbes in the patient sample and thus, in the bodily fluid of the patient from which the sample was obtained. When other technologies are used for microbial testing, the amount of time required to determine a presence of microbes may vary (e.g. from nearly instantaneously to several minutes, hours, or days). These technologies, however, are still sensitive to the inherent quality and/or integrity of the specimen that is being analyzed. Accordingly, when microbes are determined to be present in the culture medium or identified by another diagnostic test, the patient may be prescribed one or more antibiotics or other treatments specifically designed to treat or otherwise remove the undesired microbes from the patient.

Patient samples, however, can become contaminated during procurement and/or otherwise can be susceptible to false positive results. For example, microbes from a bodily surface (e.g., dermally-residing microbes) that are dislodged during needle insertion into a patient, either directly or indirectly via tissue fragments, hair follicles, sweat glands, and other skin adnexal structures, can be subsequently transferred to a culture medium with the patient sample and/or included in the specimen that is to be analyzed for non-culture based testing. Another possible source of contamination is from the person drawing the patient sample. For example, a doctor, phlebotomist, nurse, etc. can transfer contaminants from their body (e.g., finger, arms, etc.) to the patient sample and/or to the equipment containing the patient sample. Specifically, equipment and/or devices used during a patient sample procurement process (e.g., patient to needle, needle/tubing to sample vessels, etc.) often include multiple fluidic interfaces that can each introduce points of potential contamination. In some instances, such contaminants may thrive in a culture medium and/or may be identified by another diagnostic technology and eventually yield a positive microbial test result, thereby falsely indicating the presence of such microbes in vivo.

In some instances, false positive results and/or false negative results can be attributed to a specific volume of the patient sample. For example, some in vitro diagnostic (IVD) tests are sensitive to the ratio between bodily fluid collected in the sample reservoir and the preexisting contents in the sample reservoir which could include culture medium, additives (such as those described herein), and/or the like that are placed into the sample reservoir during manufacturing. In these instances, accurate results of the IVD test may depend on an appropriate amount of bodily fluid collected in the sample reservoir. For example, overfilling of volume-sensitive blood culture bottles can lead to false positive results as noted in the instructions for use and/or warning labeling from manufacturers of such culture bottles, as well as associated automated continuous monitoring microbial detection systems. On the other hand, insufficient patient sample volume within a culture medium can result in false negative results. By way of example, in a study performed by the Mayo Clinic entitled, Optimized Pathogen Detection with 30- Compared to 20-Milliliter Blood Culture Draws, Journal of Clinical Microbiology, December 2011, a patient sample volume of 20 milliliters (mL) can result in detection of about 80% of bacteremias present in a patient sample, a patient sample volume of 40 mL can result in detection of about 88% of the bacteremias, and a patient sample volume of 60 mL can result in detection of about 99% of the bacteremias. In some instances, such as in patients with sepsis, a concentration of colony forming units (CFUs) in the septic patient's bloodstream can be highly variable (including very low levels of less than 1 CFU per 10 ml of blood). Thus, ensuring that a sufficient amount of blood is collected and analyzed is desired for clinical confidence in the accuracy of the microbial test result.

While placing blood in a culture medium is a 'standard of care' today, a number of new technologies (examples of which are noted above) hold promise in increasing the pace with which microbes (and antibiotic susceptibility and/or sensitivity) can be identified in a bodily fluid sample. However, procuring a sufficient volume of blood that is analyzed remains desirable as a small volume of blood may not contain a CFU or other critical identifiable cell, biomaterial, compound, marker, organism, or the like that is actually present in the patient's bloodstream, thereby falsely indicating that a patient is not septic.

Such inaccurate results because of contamination, insufficient patient sample volume, and/or the like are a concern when attempting to diagnose or treat a suspected illness or condition. For example, false negative results from microbial tests may result in a misdiagnosis and/or delayed treatment of a patient illness, which, in some cases, could result in the death of the patient. Conversely, false positive results from microbial tests may result in the patient being unnecessarily subjected to one or more anti-microbial therapies, which may cause serious side effects to the patient including, for example, death, as well as produce an unnecessary burden and expense to the health care system due to extended length of patient stay and/or other complications associated with erroneous treatments. Additionally, the use of diagnostic imaging equipment attributable to these false positive results is also a concern from both a cost as well as patient safety perspective given the additional diagnostic procedures that are performed, potential for additional false positive or false negative results, as well as concerns around unnecessary exposure to concentrated radiation associated with a variety of imaging procedures (e.g., CT scans) has many known adverse impacts on long-term patient health.

As such, a need exists for sterile bodily fluid collection devices and methods that reduce microbial contamination in bodily fluid test samples. Additionally, a need exists for such bodily fluid collection devices to include a means for accurately verifying, measuring, and/or otherwise assessing and confirming a volume of bodily fluid transferred from a patient to a sample reservoir or culture medium that can be communicated via visual, tactile, or other means to a healthcare practitioner procuring the patient sample in substantially real-time (e.g. at the patient bedside, in an outpatient clinic or the like).

SUMMARY

Devices for parenterally procuring bodily fluid samples with reduced contamination from microbes and for volumetric verification of the bodily fluid samples are described herein. In some embodiments, an apparatus for obtaining a bodily fluid sample from a patient includes a transfer device, a sample reservoir, and a volumetric verification device. The transfer device includes a distal end portion configured to be placed in fluid communication with the patient and a proximal end portion configured to be placed in fluid communication with the sample reservoir. The volumetric verification device is disposed about a portion of the fluid reservoir such that an indicator of the volumetric verification device is associated with a predetermined or variable volume of the bodily fluid sample. By ensuring that the appropriate amount (e.g., the predetermined amount) of bodily fluid is collected into a sample reservoir for sensitive testing (e.g., IVD tests), increased sensitivity, specificity, consistency, reliability, and/or accuracy of results can be achieved, which in turn, increase clinical confidence that the results of such tests (e.g., IVD tests) are representative of the patient's in vivo condition.

DETAILED DESCRIPTION

Figure 1:
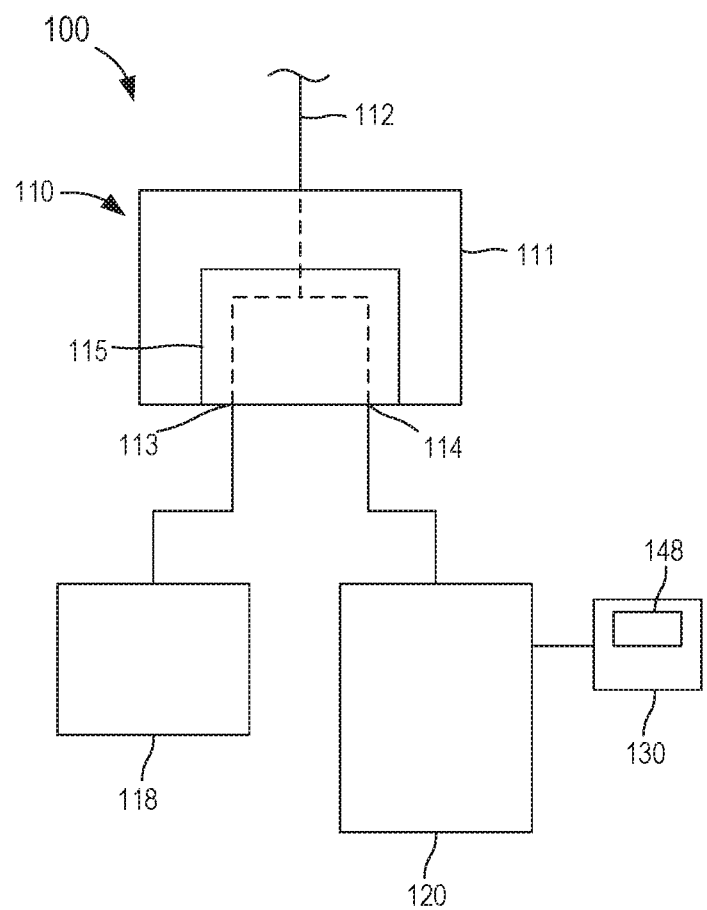
FIG. 1 is a schematic illustration of a bodily fluid collection device according to an embodiment.

Devices for parenterally procuring bodily fluid samples with reduced contamination from microbes and for volumetric verification of the bodily fluid samples are described herein. In some embodiments, a system for verifying a sample volume includes a sample reservoir and a volumetric verification device. The sample reservoir defines an inner volume and is configured to receive a volume of bodily fluid. The inner volume of the sample reservoir contains an additive. The volumetric verification device includes a first indicator and a second indicator or plurality thereof. The volumetric verification device is configured to selectively engage the sample reservoir to (1) place the first indicator in a first position along a length of the sample reservoir such that the first indicator is substantially aligned with a surface of the additive or other additive in the sample reservoir and (2) place the second indicator in a second position along the length of the sample reservoir such that the second indicator is substantially aligned with a predetermined fill volume when bodily fluid is transferred to the inner volume.

In some embodiments, a system for verifying a sample volume includes a sample reservoir and a volumetric verification device. The sample reservoir defines an inner volume and is configured to receive a volume of bodily fluid. The inner volume contains an additive. The sample reservoir includes a label having a volumetric indicator portion configured to provide an indication of a fill volume within the sample reservoir. The volumetric verification device includes a marker. The volumetric verification device is configured to selectively engage the sample reservoir to place the marker in a predetermined position along the volumetric indicator portion of the sample reservoir. The predetermined position is based the additive contained in the inner volume.

A method for verifying a sample volume of bodily fluid withdrawn from a patient using a volumetric verification device includes coupling the volumetric verification device to a sample reservoir such that an indicator of the volumetric verification device is in a predetermined position along a length of the sample reservoir. The sample reservoir defines an inner volume containing an additive. The inner volume is configured to receive a predetermined volume of bodily fluid. Fluid communication is established between the patient and the sample reservoir. A volume of bodily fluid is transferred from the patient to the sample reservoir. The method includes verifying the volume of bodily fluid transferred to the sample reservoir is substantially the predetermined volume.

In some embodiments, an apparatus for obtaining a bodily fluid sample from a patient includes a transfer device, a sample reservoir, and a volumetric verification device. The transfer device includes a distal end portion configured to be placed in fluid communication with the patient and a proximal end portion configured to be placed in fluid communication with the sample reservoir. The volumetric verification device is disposed about a portion of the fluid reservoir such that an indicator of the volumetric verification device is associated with a predetermined or variable volume of the bodily fluid sample.

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, "bodily fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof.

As used herein, the terms "first, predetermined amount," "first amount," and "first volume" describe an amount of bodily fluid configured to be received or contained by a first reservoir or a pre-sample reservoir. That is to say, the first predetermined amount refers to a desired or given amount or volume of the bodily fluid within an accepted tolerance. While the terms "first amount" and "first volume" do not explicitly describe a predetermined amount, it should be understood that the first amount and/or the first volume is the first, predetermined amount unless explicitly described differently.

As used herein, the terms "second amount" and "second volume" describe an amount of bodily fluid configured to be received or contained by a second reservoir or sample reservoir, typically after withdrawing the first predetermined volume of bodily fluid. The second amount can be any suitable amount of bodily fluid and need not be predetermined. Conversely, when explicitly described as such, the second amount received and contained by the second reservoir or sample reservoir can be a second, predetermined amount.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are in discontinuous from each other. A set of walls can also be fabricated from multiple items that are produced separately and are later joined together (e.g., via a weld, an adhesive or any suitable method).

As used herein, the terms "proximal" and "distal" refer to the direction closer to and away from, respectively, a user who would place the device into contact with a patient. Thus, for example, the end of a device first touching the body of the patient would be the distal end, while the opposite end of the device (e.g., the end of the device manipulated by the user) would be the proximal end of the device.

As used herein, the terms "about," "approximately," and "substantially" when used in connection with a numerical value convey that the value so defined is nominally the value stated. Said another way, the terms about, approximately, and substantially when used in connection with a numerical value generally include the value stated plus or minus a given tolerance. For example, in some instances, a suitable tolerance can be plus or minus 10% of the value stated; thus, about 0.5 would include any value between 0.45 and 0.55, about 10 would include any value between 9 to 11, about 1000 would include any value between 900 to 1100. In other instances, a suitable tolerance can be plus or minus an acceptable percentage of the last significant figure in the value stated. For example, a suitable tolerance can be plus or minus 10% of the last significant figure; thus, about 10.1 would include any value between 10.09 and 10.11, approximately 25 would include any value between 24.5 and 25.5. Such variance can result from manufacturing tolerances or other practical considerations (such as, for example, tolerances associated with a measuring instrument, acceptable human error, or the like).

When describing a relationship between a predetermined volume of bodily fluid and a collected volume of bodily fluid the values include a suitable tolerance such as those described above. For example, when stating that a collected volume of bodily fluid is substantially equal to a predetermined volume of bodily fluid, the collected volume and the predetermined volume are nominally equal within a suitable tolerance. In some instances, the intended use of the collected volume of bodily fluid determines the tolerance thereof. For example, in some instances, an assay of a blood culture can be about 99% accurate when the collected volume of blood is within 1.0% to 5.0% of the manufacturer's (or evidence-based best practices) recommended volume. By way of an example, a manufacturer's recommended volume for an assay of a bodily fluid can be 10 milliliters (mL) per sample collection bottle, with a total of four or six collection bottles used (i.e., an aggregate volume of 40 ml to 60 ml) plus or minus 5% for about 99% confidence. Thus, a collected volume of 10.5 mL would provide results with a confidence equal to or greater than about 99% confidence, while a collected volume of 11 mL would provide results with less than about 99% confidence. In other instances, a suitable tolerance can be 0.1%, 0.5%, 1.0%, 2.0%, 3.0%, 4.0%, 5.0%, 6.0%, 7.0%, 8.0%, 9.0%, 10.0%, or any fraction of a percent therebetween. In still other instances, a tolerance can be greater than 10.0%. Thus, any of the embodiments described herein can include and/or can be used in conjunction with any suitable flow-metering and/or volumetric verification mechanism or device that is configured to meter a fluid flow and/or otherwise measure a volume of bodily fluid within a suitable tolerance. Moreover, the flow-metering and/or volumetric verification mechanism or device can be arranged to minimize or eliminate tolerance stacking that can result from a combination of inaccurate measurement, human error, and/or the like.

The embodiments described herein include sample reservoirs and volumetric verification devices that can be used with any suitable bodily fluid transfer device. For example, in some instances, the embodiments described herein can be used with a transfer device for parenterally procuring bodily fluid samples with reduced contaminants such as, dermally residing microbes. In some embodiments, the sample reservoirs and the volumetric verification devices described herein can be used with a transfer device that is configured to divert a first, predetermined volume of bodily fluid to a pre-sample reservoir via a first flow path, and subsequently, to transfer a predetermined volume of the bodily fluid to any of the fluid reservoirs described herein, via a second flow path.

By way of example, FIG. 1 is a schematic illustration of a portion of a bodily fluid transfer system 100, according to an embodiment. Generally, the bodily fluid transfer system 100 (also referred to herein as "fluid transfer system" or "transfer system") is used to withdrawal bodily fluid from a patient such that a first portion or amount of the withdrawn fluid is diverted away from a second portion or amount of the withdrawn fluid that is to be used as a biological sample, such as for testing for the purpose of medical diagnosis and/or treatment. In other words, the transfer system 100 can transfer a first, predetermined amount of a bodily fluid to a first collection reservoir and can transfer a second amount of bodily fluid to one or more bodily fluid collection reservoirs fluidically isolated from the first collection reservoir. Moreover, the transfer system 100 can meter the second amount of bodily fluid such that a volume associated therewith is substantially a predetermined volume, as described in further detail herein.

As shown in FIG. 1, the transfer system 100 includes a transfer device 110 that is in fluid communication with a pre-sample reservoir 118 and a sample reservoir 120. The transfer device 110 can be any suitable transfer device. For example, in some embodiments, the transfer device 110 can be substantially similar to or the same as the devices included in U.S. Pat. No. 8,535,241 entitled, "Fluid Diversion Mechanism for Bodily-Fluid Sampling," filed Oct. 12, 2012 ("the '241 patent") and U.S. Pat. No. 9,060,724 entitled, "Fluid Diversion Mechanism for Bodily-Fluid Sampling," filed May 29, 2013 ("the '724 Patent") the disclosures of which are incorporated herein by reference in their entireties. In some embodiments, the transfer device 110 can include a device for metering a volumetric flow rate and/or otherwise can be substantially similar to or the same as the devices included in U.S. Patent Publication No. 2014/0155782 entitled, "Sterile Bodily-Fluid Collection Device and Methods," filed Dec. 4, 2013 ("the '782 Publication"), the disclosure of which is incorporated herein by reference in its entirety.

In the embodiment shown in FIG. 1, the transfer device 110 can include a diverter 111, a pre-sample reservoir 118, a sample reservoir 120, different from the pre-sample reservoir 118, and a flow controller 115. The diverter 111 includes an inlet port 112, a first outlet port 113, and a second outlet port 114. The inlet port 112 is coupled to and/or includes a medical device defining a pathway for withdrawing and/or conveying the bodily fluid from the patient to the transfer device 100 such as, for example, a needle, catheter, or other lumen-containing device (e.g., flexible, sterile tubing). In this manner, the diverter 111 can receive the bodily fluid from the patient via the needle, catheter, or other lumen-containing device.

The first outlet port 113 of the diverter 111 is fluidically coupled to the pre-sample reservoir 118. In some embodiments, the pre-sample reservoir 118 is monolithically formed with the first outlet port 113 and/or a portion of the diverter 111. In other embodiments, the pre-sample reservoir 118 can be mechanically and fluidically coupled to the diverter 111 via an adhesive, a resistance fit, a snap fit, a mechanical fastener, any number of mating recesses, a threaded coupling, and/or any other suitable coupling or combination thereof. Similarly stated, the pre-sample reservoir 118 can be physically (e.g., mechanically) coupled to the diverter 111 such that an interior volume defined by the pre-sample reservoir 118 is in fluid communication with the first outlet port 113 of the diverter 111. In still other embodiments, the pre-sample reservoir 118 can be operably coupled to the first outlet port 113 of the diverter 111 via an intervening structure (not shown in FIG. 1), such as a flexible, sterile tubing. More particularly, the intervening structure can define a lumen configured to place the pre-sample reservoir 118 in fluid communication with the first outlet port 113.

The second outlet port 114 of the diverter 111 is configured to fluidically couple to the sample reservoir 120. In some embodiments, the sample reservoir 120 is monolithically formed with the second outlet port 114 and/or a portion of the diverter 111. In other embodiments, the sample reservoir 120 can be mechanically coupled to the second outlet port 114 of the diverter 111 or operably coupled to the second outlet port 114 via an intervening structure (not shown in FIG. 1), such as described above with reference to the pre-sample reservoir 118. The sample reservoir 120 is configured to receive and contain the second amount of the bodily fluid. For example, the second amount of bodily fluid can be an amount withdrawn from the patient subsequent to the withdrawal of the first amount, which is fluidically isolated within the pre-sample reservoir 118.

The flow controller 115 of the transfer device 110 can be any suitable device, member, mechanism, assembly, etc. For example, the flow controller 115 can be a flow control member defining a first flow path and a second flow path, which is included in and/or otherwise disposed within a portion of the diverter 111 and movable between a first configuration to a second configuration. In some embodiments, the flow controller 115, when in the first configuration, fluidically couples the inlet port 112 to the first outlet port 113 via the first flow path. Similarly, the flow controller 115, when in the second configuration, fluidically couples the inlet port 112 to the second outlet port 114 via the second flow path. Accordingly, when the flow controller 115 is in the first configuration, the second outlet port 114 is fluidically isolated from the inlet port 112, and when the flow controller 115 is in the second configuration, the first outlet port 113 is fluidically isolated from the inlet port 112. In this manner, the flow controller 115 can direct, or divert the first amount of the bodily fluid to the pre-sample reservoir 118 via the first outlet port 113 when the flow controller 115 is in the first configuration and can direct, or divert the second amount of the bodily fluid to the sample reservoir 120 via the second outlet port 114 when the flow controller 115 is in the second configuration, as described in further detail herein. Although not shown in FIG. 1, in some embodiments, an actuator can be operably coupled to the flow controller 115 and configured to move the flow controller 115 between the first configuration and the second configuration, as described in the '724 Patent.

The pre-sample reservoir 118 of the transfer system 100 receives and contains the first, predetermined amount of the bodily fluid. More particularly, the pre-sample reservoir 118 fluidically isolates the first amount of bodily fluid contained therein from a second amount of the bodily fluid (different from the first amount of bodily fluid) subsequently withdrawn from the patient. The pre-sample reservoir 118 can be any suitable reservoir for containing a bodily fluid, such as, for example, any of those described in detail in U.S. Pat. No. 8,197,420 entitled, "Systems and Methods for Parenterally Procuring Bodily-Fluid Samples with Reduced Contamination," filed Dec. 13, 2007 ("the '420 Patent"), the disclosure of which is incorporated herein by reference in its entirety. As used in this specification, the terms "first, predetermined amount" and "first amount" describe an amount of bodily fluid received or contained by the pre-sample reservoir 118. Furthermore, while the term "first amount" does not explicitly describe a predetermined amount, the first amount is substantially the first, predetermined amount unless explicitly described differently.

The sample reservoir 120 can be any suitable reservoir(s) for containing a bodily fluid, including, for example, single use disposable collection tubes, vacuum based collection tubes, a sample reservoir as described in the '420 patent incorporated by reference above, and/or the like. In some embodiments, the sample reservoir 120 can be substantially similar to or the same as known sample containers such as, for example, a Vacutainer® (manufactured by BD), a BacT/ALERT® SN or BacT/ALERT® FA (manufactured by Biomerieux, Inc.), a Nanotainer™ (manufactured by Theranos), and/or any suitable reservoir, vial, microvial, microliter vial, container, microcontainer, and/or the like. In such embodiments, the sample reservoir 120 can include a vacuum seal that maintains negative pressure conditions (vacuum conditions) inside the sample reservoir 120, which in turn, can facilitate withdrawal of bodily fluid from the patient, through the diverter 111, and into the sample reservoir 120, via a vacuum or suction force, as described in further detail herein. In some embodiments, the sample reservoir 120 can be any suitable sample or culture bottle such as, for example, an aerobic culture bottle or an anaerobic culture bottle and the transfer system 100 can be used to collect multiple aerobic and/or multiple anaerobic blood culture samples from a single venipuncture or single connection to an intravenous, central line and/or similar type of indwelling catheter. In this manner, the culture bottle can receive a bodily fluid sample, which can then be tested (e.g., via in vitro diagnostic (IVD) tests, and/or any other suitable test) for the presence of, for example, Gram-Positive bacteria, Gram-Negative bacteria, yeast, and/or any other organism and subsequently tested using, for example, a polymerase chain reaction (PCR)-based system to identify a specific organism. In some instances, the culture bottle can receive a bodily fluid sample and the culture medium (disposed therein) can be tested for the presence of any suitable organism. If such a test of the culture medium yields a positive result, the culture medium can be subsequently tested using a PCR-based system to identify a specific organism.

As used herein, the term "second amount" describes an amount of bodily fluid received or contained by the sample reservoir 120. In some embodiments, the second amount can be any suitable amount of bodily fluid and need not be predetermined. In other embodiments, the second amount received and contained by the sample reservoir 120 is a second, predetermined amount. Moreover, in some embodiments, the second, predetermined amount can be associated with a desired volume of bodily fluid plus or minus a tolerance for use in any suitable testing method or the like. That is to say, in some instances, the second amount of bodily fluid transferred into the sample reservoir 120 can have a volume that is substantially equal to a desired volume for any given testing procedure such as, for example, microbial testing and/or the like. In some embodiments, the sample reservoir 120 can be transparent such that the user can have visual feedback to confirm bodily fluid flow into the sample reservoir 120. In some embodiments, the second amount of bodily fluid can be any suitable volume of bodily fluid from, for example, one or a few drops of bodily fluid (e.g., nanoliters or microliters) to 10 milliliters (mL), 20 ml, 30 mL, 40 mL, 50 mL, 100 mL, 1,000 mL, 10,000 mL, or more (or any value or fraction of a value therebetween) of bodily fluid.

In some embodiments, the sample reservoir 120 can include, for example, any suitable additive, culture medium, substances, and/or the like. For example, in some embodiments, the sample reservoir 120 can include an aerobic or anaerobic culture medium (e.g., a growth medium or the like), which occupies at least a portion of the inner volume defined by the sample reservoir 120. In some embodiments, the sample reservoir 120 can include, for example, any suitable additive or the like such as, heparin, citrate, ethylenediaminetetraacetic acid (EDTA), oxalate, and/or the like, which similarly occupies at least a portion of the inner volume defined by the sample reservoir 120. In some instances, the size, density, volume, and/or the like of the additive and/or culture medium that are commonly found in sample reservoirs can vary based on, for example, tolerances, constituent substances comprising the additive, and/or the type of testing to be performed. Thus, the additive and/or the culture medium disposed in the inner volume and a volume of bodily fluid transferred into the sample reservoir collectively define a total volume and/or a total fill volume within the sample reservoir 120. In other words, in some instances, determining a volume of bodily fluid transferred into a sample reservoir may include accounting for a portion of a total volume attributable to a culture medium and/or additive.

While the term "culture medium" can be used to describe a substance configured to react with organisms in a bodily fluid (e.g., microorganisms such as bacteria) and the term "additive" can be used to describe a substance configured to react with portions of the bodily fluid (e.g., constituent cells of blood, serum, synovial fluid, etc.), it should be understood that a sample reservoir can include any suitable substance, liquid, solid, powder, lyophilized compound, gas, etc. Moreover, when referring to an "additive" within a sample reservoir, it should be understood that the additive could be a culture medium, such as an aerobic culture medium and/or an anaerobic culture medium contained in a culture bottle, an additive and/or any other suitable substance or combination of substances contained in a culture bottle and/or any other suitable reservoir such as those described above. That is to say, the embodiments described herein can be used with any suitable fluid reservoir or the like containing any suitable substance to accurately determine a volume of bodily fluid transferred into the fluid reservoir.

As shown in FIG. 1, the volumetric verification device 130 is configured to engage (e.g., couple to, be disposed about, align with, and/or the like) the sample reservoir 120 to provide an indication to a user associated with a volume of bodily fluid disposed within the sample reservoir 120. As used herein, the volumetric verification device 130 refers to a device used to indicate an existing volume of bodily fluid. That is to say, the volumetric verification device 130 is used to indicate a bulk volume or the like. The volumetric verification device 130 (also referred to herein as "verification device") can be any suitable device, member, mechanism, assembly, etc. configured to provide a user with an indicator associated with a volume of the bodily fluid disposed within the sample reservoir 120. For example, in some embodiments, the verification device 130 can be disposed about a portion of the sample reservoir 120 and can include an indicator 148 or the like configured to provide a visual indication of a volume of bodily fluid within the sample reservoir 120. In some embodiments, the indicator 148 of the verification device 130 can provide a visual indication of a volume of the bodily fluid within the sample reservoir 120 relative to and/or at least partially associated with, the culture medium or other additive(s) disposed therein, as described in further detail with reference to specific embodiments.

In some embodiments, the transfer system 100 can optionally include one or more flow-metering devices that can meter a flow of bodily fluid through the collection device. For example, a flow-metering device can be in fluid communication with the first fluid flow path and/or the second fluid flow path to meter a flow of bodily fluid through the diverter 111 of the transfer device 110. In other embodiments, a flow-metering device can be in fluid communication with and/or otherwise disposed in the first port 113 and/or the second port 114. In still other embodiments, the flow-metering device can be in fluid communication with an inlet port or the like of the sample reservoir 120. Moreover, the flow-metering device can include an indicator or the like (e.g., a dial, a display, color, a haptic output device, an electrical signal output device such as a wireless radio signal, Bluetooth radio signal, etc.) that can be configured to provide an indication to a user that is associated with a predetermined volume being transferred to the pre-sample reservoir 118 and/or the sample reservoir 120. In some embodiments, the flow-metering device can be operably coupled to, for example, an actuator or the like, which can move the flow controller 115 between its first configuration and its second configuration based on a desired volume of bodily fluid having passed through the flow-metering device. Thus, the flow-metering device can be used to ensure a desired volume of bodily fluid is transferred to the pre-sample reservoir 118 and/or the sample reservoir 120 and can be used in conjunction with, for example, the verification device 130. For example, in some embodiments, the sample reservoir 120 and the verification device 130 can be used with and/or fluidically coupled to, the transfer device and/or collection devices described in detail in the '782 Publication.

Figure 2:
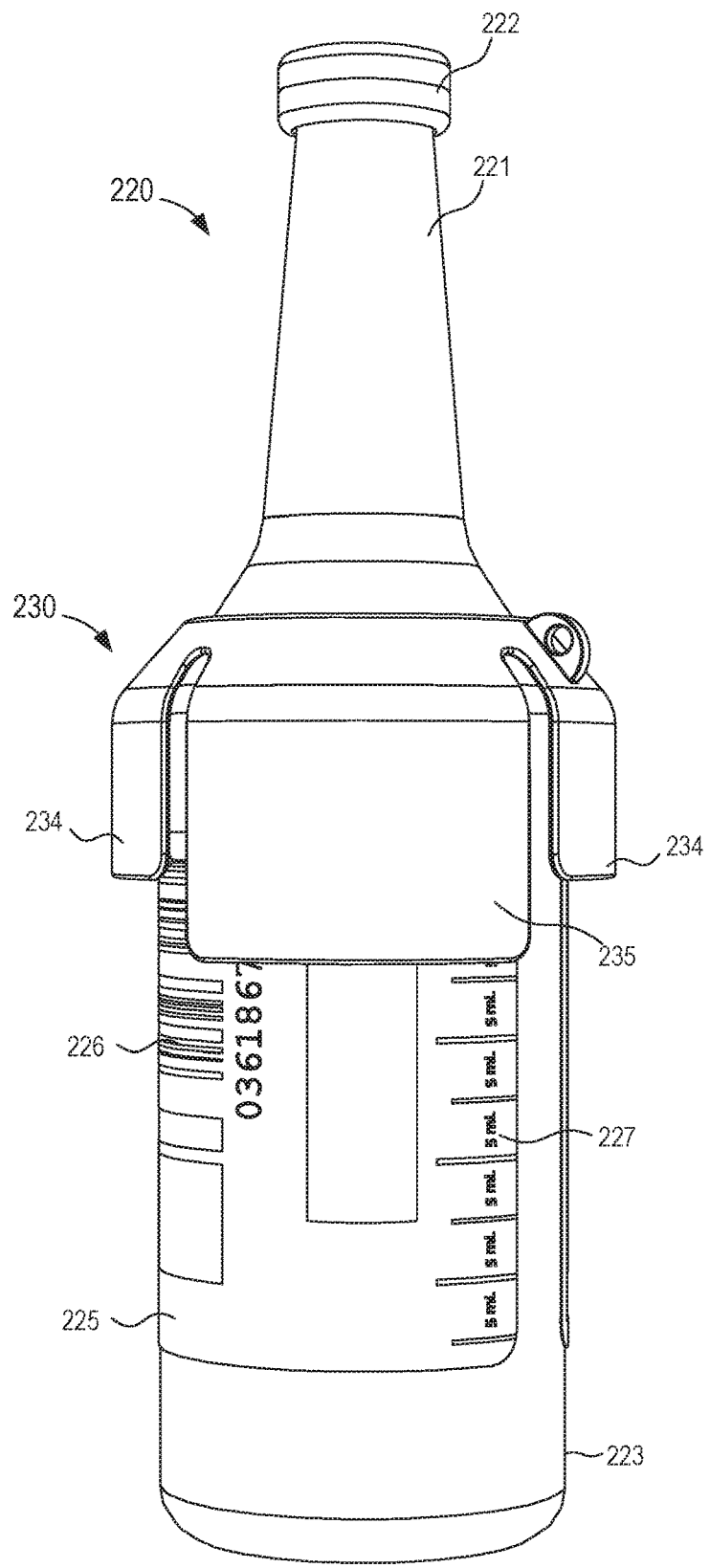
FIGS. 2-4 are various views of a sample reservoir and a volumetric verification device according to an embodiment.
Figure 4:
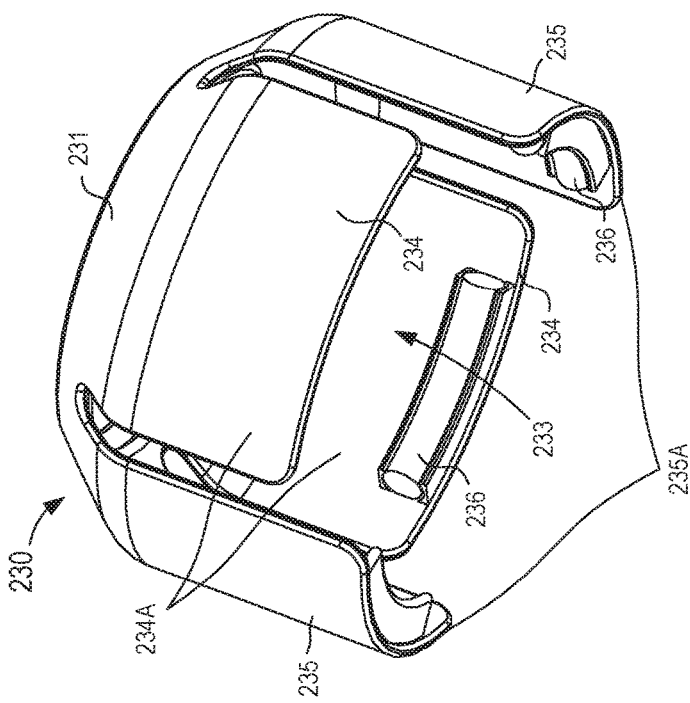
Figure 3:
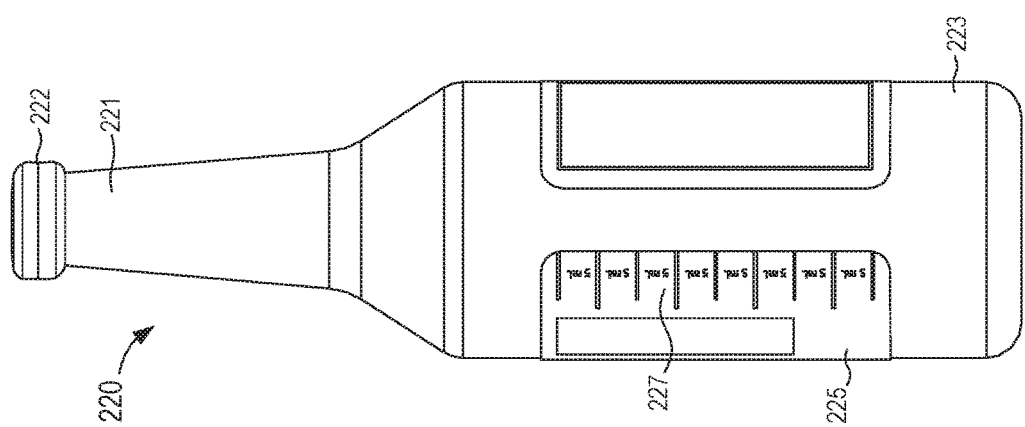

FIGS. 2-10 illustrate various embodiments of sample reservoirs and volumetric verification devices that can be used, for example, in the transfer system 100 described above. In some instances, the embodiments of the sample reservoirs described herein can be placed in fluid communication with, for example, bodily fluid transfer devices and/or bodily fluid collection devices such as those described in the '724 Patent and/or the '782 Publication. By way of example, FIGS. 2-4 illustrate a sample reservoir 220 and a volumetric verification device 230, according to an embodiment. Although not shown in FIGS. 2-4, the sample reservoir 220 and the volumetric verification device 230 can be used with any suitable bodily fluid transfer device and/or bodily fluid collection device such as the transfer device 110 and/or the devices described in the '724 Patent and/or the '782 Publication. That is to say, the sample reservoir 220 can receive, from a transfer device, a flow of bodily fluid (e.g., blood) with reduced contaminants such as, for example, dermally residing microbes and/or the like, as described in further detail herein.

As shown in FIGS. 2 and 3, the sample reservoir 220 includes a proximal end portion 221 and a distal end portion 223 and defines an inner volume (not shown). The proximal end portion 221 includes a port 222 configured to receive an adapter, a puncture member, a coupler, a locking member and/or the like. In some embodiments, the port 222 can be, for example, a self-healing port or the like. In some embodiments, the port 222 can be a vacuum seal configured to maintain a vacuum condition within the inner volume until the port 222 is coupled to and/or punctured by an outlet portion or adapter of a transfer device.

The sample reservoir 220 can be any suitable reservoir for containing a bodily fluid, including, for example, single use disposable collection reservoir, vacuum based collection reservoir (e.g., maintaining negative pressure conditions that can produce a suction or vacuum force), a sample reservoir as described in the '420 patent incorporated by reference above, and/or the like. Moreover, while shown in FIGS. 2 and 3 as having a bottle shape or the like, the sample reservoir can be any suitable bottle, tube, vial, microvial, container, syringe, etc. As described above, in some embodiments, the reservoir 220 can be an aerobic culture bottle or an anaerobic culture bottles. That is to say, the sample reservoir 220 can include an aerobic or anaerobic culture medium disposed within an inner volume defined by the sample reservoir 220. Moreover, the culture medium disposed therein can be associated with one or more tests, procedures, and/or actions configured to, for example, detect the presence of certain microbes that are known to thrive in that medium. In other embodiments, the sample reservoir 220 can include common additives such as heparin, citrate, EDTA, oxalate and/or the like that are used to preserve specific characteristics and/or qualities of a bodily fluid sample (e.g., blood) prior to diagnostic analysis.

Similarly, in some embodiments, the sample reservoir 220 is configured to receive a predetermined volume of bodily fluid, which can be associated with a test or the like to be performed thereon. For example, as shown in FIG. 3, the sample reservoir 220 includes a label 225, tag, or indicia disposed about the outside of the sample reservoir 220. The label 225 includes, for example, a code portion 226 and a volumetric indicator portion 227. The code portion 226 can be, for example, a bar code, a quick response (QR) code, a radio-frequency identification (RFID) tag, a near field communication (NFC) tag, and/or the like. In some embodiments, the code portion 226 can include a serial number. In this manner, the code portion 226 can provide a user (e.g., a doctor, phlebotomist, nurse, technician, etc.) with information associated with the sample reservoir 220 such as, for example, the type of culture medium disposed therein, the amount (e.g., volume, mass, density, etc.) of the culture medium disposed therein, a volume of bodily fluid that the sample reservoir 220 should receive, a tolerance value, the type of tests to be performed on the bodily fluid sample disposed therein, and/or the like. Thus, the user can determine, inter alia, the amount or the volume of bodily fluid that he or she should transfer into the sample reservoir 220.

The volumetric indicator portion 227 can provide a visual indicator associated with the bodily fluid disposed in the sample reservoir 220. For example, the volumetric indicator portion 227 can include a set of evenly spaced lines, tic marks, dashes, arrows, markers, and/or any other suitable gradation or indicia that can be associated with a specific volume of the sample reservoir 220 if filled to that point. In some embodiments, the sample reservoir 220 can be substantially transparent, thereby allowing the user to visualize the sample disposed therein. Thus, the user can assess the volume of the bodily fluid disposed in the sample reservoir 220 by determining at what point along the indicator portion 227 that surface and/or meniscus of the bodily fluid aligns. In some instances, however, the culture medium disposed within the sample reservoir can affect the representation of the volume of bodily fluid disposed therein. For example, an amount of culture medium disposed in the sample reservoir 220 can vary based on the type of medium, the type of test with which the medium is associated, tolerances associated with the amount of the medium, and/or the like. Thus, as shown in FIG. 2, the volumetric verification device 230 can be configured to engage the sample reservoir 220 to meter, measure, and/or otherwise indicate to a user, the volume of the bodily fluid disposed in the sample reservoir 220.

The volumetric verification device 230 (also referred to herein as "verification device") can be any suitable device, member, mechanism, assembly, etc. configured to provide a user with an indicator associated with a volume of the bodily fluid disposed within the sample reservoir 220. In some embodiments, the verification device 230 can have a size and/or shape that substantially corresponds to the sample reservoir 220. For example, the verification device 230 can be a substantially annular ring or the like that defines an inner volume 236 configured to receive a portion of the sample reservoir 220. In other embodiments, the verification device 230 can be any suitable shape such as, for example, polygonal, oblong, and/or the like. In this manner, the verification device 230 can be disposed about a portion of the sample reservoir 220 such that a portion of the sample reservoir 220 is disposed in the inner volume 233, as shown in FIG. 2. More specifically, the verification device 230 can have a shape that substantially corresponds to a shape of the sample reservoir 220 such that when the verification device 230 is disposed about the sample reservoir 220, the verification device 230 is substantially in a predetermined position relative to the sample reservoir 220. Said another way, the verification 230 can be configured such that when the verification device 230 is disposed about any sample reservoir having a shape that substantially corresponds to the shape of the sample reservoir 220, the verification device 230 is disposed in substantially the same relative position along that sample reservoir.

As shown in FIGS. 2 and 4, the verification device 230 includes a first set of tabs 234A and a second set of tabs 235A that extend from a proximal end portion 231 of the verification device 230. The first set of tabs 234A includes, for example, a pair of tabs 234 that are arranged opposite each other. Similarly, the second set of tabs 235A includes, for example, a pair of tabs 235 (different from the pair of tabs 234 of the first set of tabs 234A) that are arranged opposite each other. In this embodiment, the first set of tabs 234A and the second set of tabs 235A extend from the proximal end portion 231 in an alternating configuration. In other embodiments, the first set of tabs 234A and the second set of tabs 235A can be arranged in any suitable manner. The first set of tabs 234A and the second set of tabs 235A collectively define at least a portion of the inner volume 233 such that when the verification device 230 is disposed about the sample reservoir 220, the first set of tabs 234A and the second set of tabs 235A are disposed adjacent to an outer surface of the sample reservoir 220.

As shown in FIGS. 2 and 4, the first set of tabs 234A extend from the proximal end portion 231 a first distance and the second set of tabs 235A extend from the proximal end portion 231 a second distance, greater than the first distance. Accordingly, when the verification device 230 is disposed about a portion of the sample reservoir 220, an end portion of each tab 234 in the first set of tabs 234A (i.e., opposite the proximal end portion 231) is disposed at a first position along a length of the sample reservoir 220. Similarly, an end portion of each tab 235 in the second set of tabs 235A (i.e., opposite the proximal end portion 231) is disposed at a second position along a length of the sample reservoir 220, different from the first position.

In some embodiments, the first position and the second position can be associated with, for example, a desired fill volume of the sample reservoir 220. For example, while a sample reservoir may have substantially the same shape and size as another sample reservoir, such sample reservoirs can include different culture mediums and/or the like, each of which can be associated with, for example, a different fill height for substantially the same fill volume. Thus, with the verification device 230 disposed in a substantially predetermined position about the sample reservoir 220 (as described above), the first set of tabs 234 and the second set of tabs 235 can be associated with a desired fill height associated with a desired fill volume. More specifically, in this embodiment, the first set of tabs 234A can be associated with a fill height corresponding to a fill volume of about 8 mL to about 10 mL when the sample reservoir 220 includes an anaerobic culture medium. Similarly, the second set of tabs 235A can be associated with a fill height corresponding to a fill volume of about 8 mL to about 10 mL when the sample reservoir 220 includes an aerobic culture medium. In other embodiments, a desired fill height can be associated with any suitable fill volume such as, for example, a "micro" sample of just a few drops of blood (less than 1 ml), about 1 mL, about 2 mL, about 3 mL, about 4 mL, about 5 mL, about 6 mL, about 7 mL, or more.

As shown in FIG. 4, each tab 234 in the first set of tabs 234A and each tab 235 in the second set of tabs 235A includes an indicator 236 disposed at or near the end portion of the tabs 234 and/or 235. The indicators 236 can be any suitable shape, size, or configuration and can selectively engage the sample reservoir 220. For example, when an indicator 236 of a tab 234 or 235 is placed in contact with the outer surface of the sample reservoir 220, the indicator 236 can mark, score, scribe, scrape, indent, and/or otherwise change a corresponding portion of the outer surface. In other words, the indicators 236 can each be a marker, a protrusion, a pointed surface, a cutting or scraping surface, and/or the like. Thus, the indicator 236 of a tab 234 or 235 can engage the outer surface of the sample reservoir 220 to provide, for example, a visual indication on the outer surface of the sample reservoir 220 associated with the position of that indicator 236.

In use, a user can position the verification device 230 about the sample reservoir 220 that includes, for example, an anaerobic culture medium. Once in a desired position, the user can exert a force on at least one tab 235 of the second set of tabs 235 such that the indicator 236 disposed on the inner surface of that tab(s) 235 engages the outer surface of the sample reservoir 220. In this manner, the user can rotate the verification device 230 about the sample reservoir 220, which in turn, results in the indicator(s) 236 of the second set of tabs 235 providing a visual indication on the sample reservoir 220 associated with a desired fill volume of about 8 mL to about 10 mL corresponding to the anaerobic culture medium disposed in the sample reservoir 220. In some embodiments, the visual indication (e.g., the mark, line, etc.) can be associated with and/or can be disposed along the volume indicator portion 227 of the label 225. Thus, the volume indicator portion 227 can provide an indication of, for example, an absolute volume within the sample reservoir 220 and/or a volume of bodily fluid within the sample reservoir relative to the culture medium disposed therein. After providing, forming, and/or otherwise making the visual indication on the outer surface of the sample reservoir 220, the user can then transfer a bodily fluid into the sample reservoir (e.g., via any suitable transfer device described herein) and can stop the transfer of bodily fluid when a volume of the bodily fluid is substantially equal to the predetermined volume associated with the visual indication on the sample reservoir.

Similarly, a user can position the verification device 230 about the sample reservoir 220 that includes, for example, an aerobic culture medium and can exert a force on at least one tab 234 of the second set of tabs 234A. Thus, when the user rotates the verification device 230 about the sample reservoir 220, the indicator 236 disposed on the tab(s) 234 provide a visual indication on the sample reservoir 220 associated with a desired fill volume of about 8 mL to about 10 mL corresponding to the aerobic culture medium disposed in the sample reservoir 220. The user can then transfer a bodily fluid into the sample reservoir (e.g., via any suitable transfer device described herein) and can stop the transfer of bodily fluid when a volume of the bodily fluid is substantially equal to the predetermined volume associated with the visual indication on the sample reservoir.

Although not shown in FIGS. 2-4, in some embodiments, the first set of tabs 234A and the second set of tabs 235A can include, for example, indicia, a symbol, a color-coding, and/or the like associated with the type of sample reservoir 220 with which that set of tabs corresponds. For example, in some embodiments, the sample reservoir 220 can include a color-coding or the like that can provide an indication of the contents of that sample reservoir 220 (e.g., aerobic or anaerobic). Thus, when the user positions the verification device 230 about the sample reservoir 220, the user can engage the set of tabs 234 or 235 having a similar color-coding. In other embodiments, the sample reservoir 220 and the set of tabs 234 and 235 can provide any suitable visual indication configured to indicate a relationship between the first set of tabs 234 and the sample reservoir 220 or the second set of tabs 235 and the sample reservoir 220. In some embodiments, the label 225 can be similarly color-coded, which can allow a user to match the color-coding and/or to otherwise engage the tabs 234 or 235 having the matching color.

Figure 5:
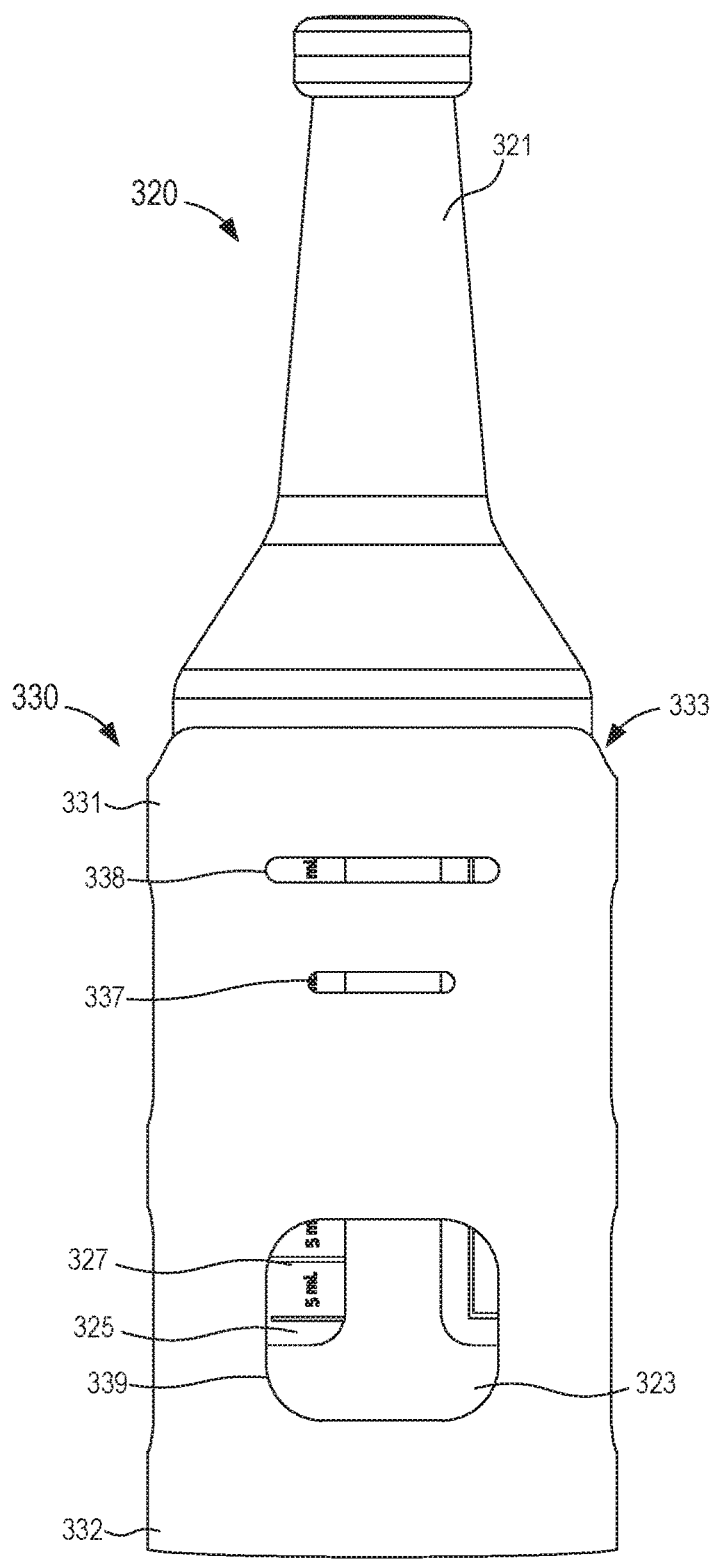
FIG. 5 is a front view of a sample reservoir and a volumetric verification device according to an embodiment.

While the volumetric verification device 230 is particularly shown and described above with reference to FIGS. 2 and 4, in other embodiments, any suitable volumetric verification device can be disposed about a sample reservoir to provide, for example, a visual indicator associated with a desired fill volume of the sample reservoir. For example, FIG. 5 illustrates a verification device 330 disposed about a sample reservoir 320, according to an embodiment. The sample reservoir 320 can be any suitable reservoir configured to receive a bodily fluid such as, for example, those described herein. For example, the sample reservoir 320 includes at least a proximal end portion 321, a distal end portion 322, and a label 325 including a volume indicator portion 327. In this embodiment, the sample reservoir 320 can be substantially similar to or the same as the sample reservoir 220 described in detail above with reference to FIGS. 2-4. Thus, the sample reservoir 320 is not described in further detail herein.

The volumetric verification device 330 (also referred to herein as "verification device 330") includes a proximal end portion 331 and a distal end portion 332, and defines an inner volume 333. The verification device 330 can be any suitable device, member, mechanism, assembly, etc. configured to provide a user with an indicator associated with a volume of the bodily fluid disposed within the sample reservoir 320. In some embodiments, the verification device 330 can have a size and/or shape that substantially corresponds to the sample reservoir 320. For example, the verification device 330 can include an annular wall extending from a base and defining an inner volume (not shown in FIG. 5). Said another way, the verification device 330 can be a sleeve or the like configured to be disposed about a portion of the sample reservoir 320. More specifically, the verification device 330 can be disposed about the sample reservoir 320 such that the distal end portion 332 of the verification device 330 (e.g., a base or the like) is in contact with the distal end portion 323 of the sample reservoir 320 and as such, is substantially in a predetermined position relative to the sample reservoir 320. Said another way, the verification device 330 can be configured such that when the verification device 330 is disposed about any sample reservoir having a shape that substantially corresponds to the shape of the sample reservoir 320, the verification device 330 is disposed in substantially the same relative position along that sample reservoir. Simply stated, the verification device 330 can be positioned about the sample reservoir 320 such that a distal surface of the sample reservoir 320 (not shown in FIG. 5) is in contact with a distal, inner surface of the verification device 330.

The verification device 330 defines a first opening 337, a second opening 338, and a viewing window 339. The viewing window 339 can be any suitable shape and/or size and can allow a user to visualize a portion of the sample reservoir 320 when the verification device 330 is disposed about the sample reservoir 320. In other embodiments, the verification device 330 need not define the viewing window 339. Although not shown in FIG. 5, the verification device 330 can also define an identification window or the like configured to substantially align with an identification portion of the sample reservoir 320 such as, for example, a serial number, bar code, QR code, and/or the like (described above with reference to the sample reservoir 220). Thus, the identification window can allow visualization of the identification portion when the sample reservoir 320 is disposed in the verification device 330.

The first opening 337 and the second opening 338 can be any suitable shape, size, and/or arrangement. As shown in FIG. 5, the first opening 337 and the second opening 338 can be, for example, slots that extend along a portion of the circumference of the verification device 330. While the first opening 337 is shown as being smaller than the second opening 338, in other embodiments, the first opening 337 and the second opening 338 can have substantially the same shape and/or size or the first opening 337 can be larger than the second opening 338. In this manner, the first opening 337 and the second opening 338 can allow a user to visualize a portion of the sample reservoir 320 when the sample reservoir 320 is disposed therein.

When the verification device 330 is disposed about a desired portion of the sample reservoir 320 (as described above), the first opening 337 is disposed at a first position along a length of the sample reservoir 320, and the second opening 338 is disposed at a second position along a length of the sample reservoir 320, different from the first position. In some embodiments, the first position and the second position can be associated with, for example, a position of a culture medium within the sample reservoir 320 and a desired fill volume of the sample reservoir 320, respectively. For example, while a sample reservoir may have substantially the same shape and size as another sample reservoir, such sample reservoirs can include different culture mediums and/or the like, each of which can be associated with, for example, a different fill height for substantially the same fill volume. Said another way, the first opening 337 and the second opening 338 are spaced apart by a predetermined and/or desired distance such that when the verification device 330 is disposed about a desired portion of the sample reservoir 320, a portion of the inner volume of the sample reservoir 320 is defined therebetween. In some embodiments, this portion of the inner volume of the sample reservoir 320 is substantially equal to a volume of the culture medium. In other words, the culture medium has substantially the same volume as the portion of the inner volume of the sample reservoir 320 defined between the first opening 337 and the second opening 338. In this manner, the predetermined and/or desired fill height and/or volume is equal to and/or based on a sum of a volume of bodily fluid transferred into the inner volume and a volume of the culture medium.

In some embodiments, with the verification device 330 disposed in a substantially predetermined position about the sample reservoir 320 (as described above) the first opening 337 can, for example, correspond with a height of a culture medium disposed in the sample reservoir 320 and the second opening 338 can be associated with a desired fill volume corresponding to that culture medium. More specifically, the first opening 337 can allow for visualization of a culture medium and the second opening 338 can be associated with and/or can allow for visualization of a fill height and/or a fill volume of about 8 mL to about 10 mL respective to the culture medium disposed therein. In this manner, the verification device 330 can be configured to correspond to a given sample reservoir based at least in part on the relative position of the first opening 337 and the second opening 338. For example, a first verification device can define a first opening and a second opening at a first position associated with a fill volume of about 8 mL to about 10 mL relative to an anaerobic culture medium, while a second verification device can define a first opening and a second opening at a second position associated with a fill volume of about 8 mL to about 10 mL relative to an aerobic culture medium. In other embodiments, a verification device can include any number of openings associated with various points of interest within the sample reservoir.

In use, a user can position the verification device 330 about the sample reservoir 320 that includes, for example, an anaerobic or an aerobic culture medium. Once in a desired position, the user can visualize the culture medium via the first opening 337 and a portion of the inner volume of the sample reservoir 320 associated with a desired fill volume of about 8 mL to about 10 mL corresponding to the anaerobic or aerobic culture medium disposed therein. In some embodiments, the first opening 337 and the second opening 338 can allow for visualization of a portion of the volume indicator portion 327 of the label 325. Thus, the volume indicator portion 327 can provide an indication of, for example, an absolute volume within the sample reservoir 320 and/or a volume of bodily fluid within the sample reservoir 320 relative to the culture medium disposed therein. With the verification device 330 in the desired position, the user can then transfer a bodily fluid into the sample reservoir 320 (e.g., via any suitable transfer device described herein) and can stop the transfer of bodily fluid when a volume of the bodily fluid is visible via the second opening 338. Thus, a predetermined volume of bodily fluid can be transferred to the sample reservoir 320.

Although not shown in FIG. 5, in some embodiments, the verification device 330 can include, for example, indicia, a symbol, a color-coding, and/or the like associated with the type of sample reservoir 320 with which the verification device 330 (e.g., the openings 337 and 338) corresponds. For example, in some embodiments, the sample reservoir 320 can include a color-coding or the like that can provide an indication of the contents of that sample reservoir 320 (e.g., aerobic or anaerobic) and the corresponding verification device 330 can include a similar color-coding or the like. In other embodiments, the sample reservoir 320 and/or the verification device 330 can provide any suitable visual indication configured to indicate a relationship therebetween.

While not shown in FIG. 5, in some embodiments, the verification device 330 can include any suitable adjustment mechanism or the like configured to adjust the position of the verification device 330 relative to the sample reservoir 320. For example, as described above, the verification device 330 can be disposed about the sample reservoir 320 such that the distal surface of the sample reservoir 320 is in contact with the distal, inner surface of the verification device 330. In some embodiments, however, the distal, inner surface can be an adjustable surface configured to move in a proximal or distal direction in response to a user input. For example, in some embodiments, the surface can be coupled to a screw or threaded coupling or platform. In such embodiments, the user can manipulate an engagement portion or the like (not shown) to rotate the screw or threaded coupling, which in turn, can move the distal, inner surface in the proximal or the distal direction. Thus, with the distal surface of the sample reservoir 320 in contact with the adjustable inner surface of the verification device 330, the user can adjust the position of the sample reservoir 320 relative to, for example, the first opening 337 and the second opening 338.

In some embodiments, this adjustment can account for manufacturing tolerances associated with the sample reservoir 320, verification device 330, and/or additive contained in the sample reservoir 320. For example, in some embodiments, the additive can include a $CO_2$ detection element or substance that can have a variable height or volume while the remaining portions of the additive otherwise have a predetermined size and/or volume (e.g., within a given tolerance). Thus, the user can manipulate the engagement portion and/or any suitable portion of an adjustment mechanism to account for such variances. Moreover, by having a fixed distance between the first opening 337 and the second opening 338 and by aligning the first opening with a top surface or meniscus of the additive, filling the sample reservoir 320 with a volume of bodily fluid until the top surface or meniscus of the bodily fluid is aligned with the second opening 338 will result in a predetermined ratio between the bodily fluid volume and the volume of the additive regardless of the variances described above. Although described above as being a screw or threaded coupling, an adjustment mechanism or the like can be any suitable device or combination of devices (e.g., a slider, wedge, spring, handle, etc.).

Figure 6:
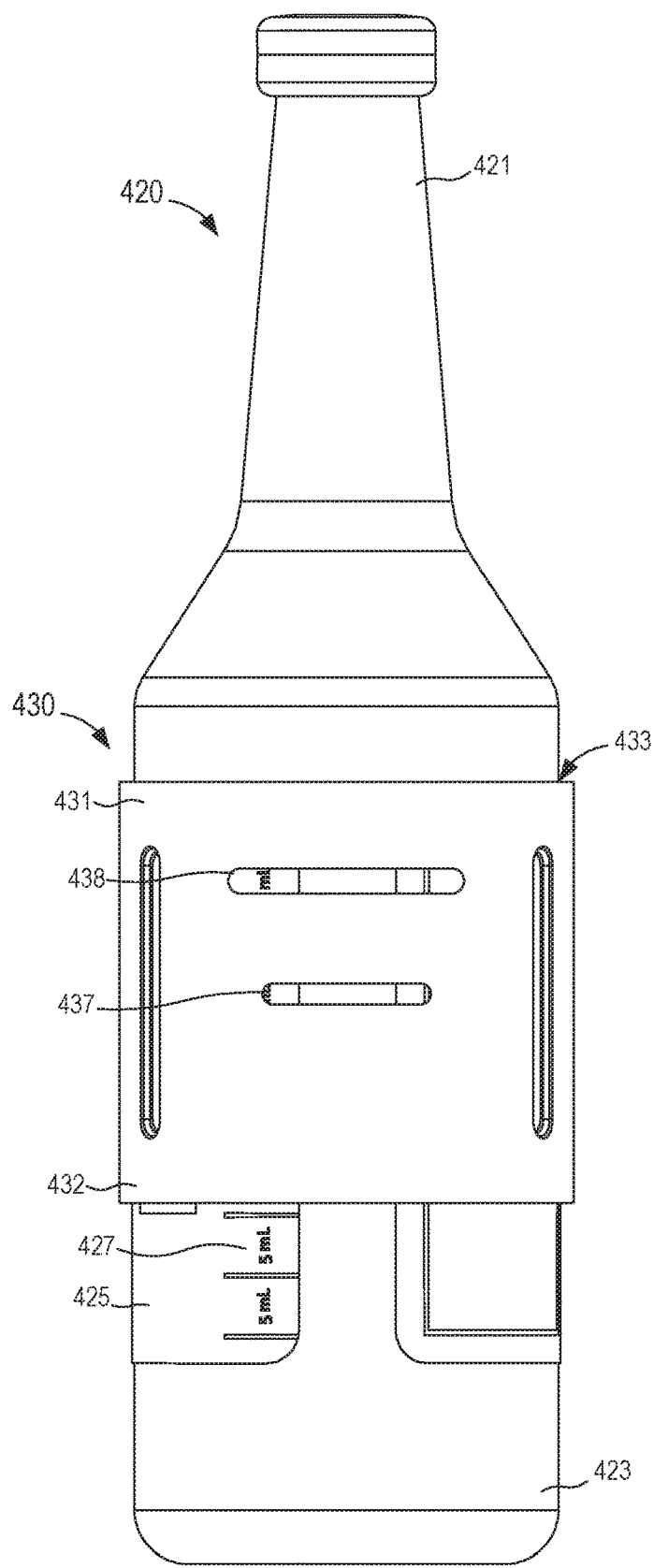
FIG. 6 is a front view of a sample reservoir and a volumetric verification device according to an embodiment.

While the volumetric verification device 330 is particularly shown and described above with reference to FIG. 5, in other embodiments, any suitable volumetric verification device can be disposed about a sample reservoir to provide, for example, a visual indicator associated with a desired fill volume of the sample reservoir. For example, FIG. 6 illustrates a volumetric verification device 430 disposed about a sample reservoir 420, according to an embodiment. The sample reservoir 420 can be any suitable reservoir configured to receive a bodily fluid such as, for example, those described herein. For example, the sample reservoir 420 includes at least a proximal end portion 421, a distal end portion 422, and a label 425 including a volume indicator portion 427. In this embodiment, the sample reservoir 420 can be substantially similar to or the same as the sample reservoir 220 described in detail above with reference to FIGS. 2-4. Thus, the sample reservoir 420 is not described in further detail herein.

The volumetric verification device 430 (also referred to herein as "verification device 430") includes a proximal end portion 431 and a distal end portion 432, and defines an inner volume 433. The verification device 430 can be any suitable device, member, mechanism, assembly, etc. configured to provide a user with an indicator associated with a volume of the bodily fluid disposed within the sample reservoir 420. For example, the verification device 430 can be substantially similar to the verification device 330 described above with reference to FIG. 5; thus, some aspects of the verification device 430 are not described in further detail herein. For example, as shown in FIG. 6, the verification device 430 defines a first opening 437 and a second opening 438. In some embodiments, the first opening 437 and the second opening 438 can be substantially similar in form and function to the first opening 337 and the second opening 338 of the verification device 330.

The verification device 430 can differ from the verification device 330, however, by being and/or having a shorter length and a substantially open distal end portion 432. That is to say, the verification device 430 is, for example, a sleeve disposed about a portion of the sample reservoir 420. In some embodiments, such an arrangement can allow the verification device 430 to be moved along a length of the fluid reservoir 420. Specifically, in use, a user can position the verification device 430 about the sample reservoir 420 such that a top surface of a culture medium disposed in the sample reservoir 420 is at least partially aligned with and viewable through the first opening 437. As such, the second opening 438 can be associated with a desired fill volume of the sample reservoir 420 relative to the culture medium disposed therein. Similarly stated, the position of the second opening 438 is based, at least in part, on the position of the first opening 437. In some instances, the position of the second opening 438 can be associated with and/or can allow for visualization of a fill height and/or a fill volume of about 8 mL to about 10 mL respective to the culture medium disposed therein. In addition, the second opening 438 can allow for visualization of the indicator portion 427 of the sample reservoir 420. Thus, the volume indicator portion 427 can provide an indication of, for example, an absolute volume within the sample reservoir 420 and/or a volume of bodily fluid within the sample reservoir 420 relative to the culture medium disposed therein. With the verification device 430 in the desired position, the user can then transfer a bodily fluid into the sample reservoir 420 (e.g., via any suitable transfer device described herein) and can stop the transfer of bodily fluid when a volume of the bodily fluid is visible via the second opening 438. Thus, a predetermined volume of bodily fluid can be transferred to the sample reservoir 420.

Figure 7:
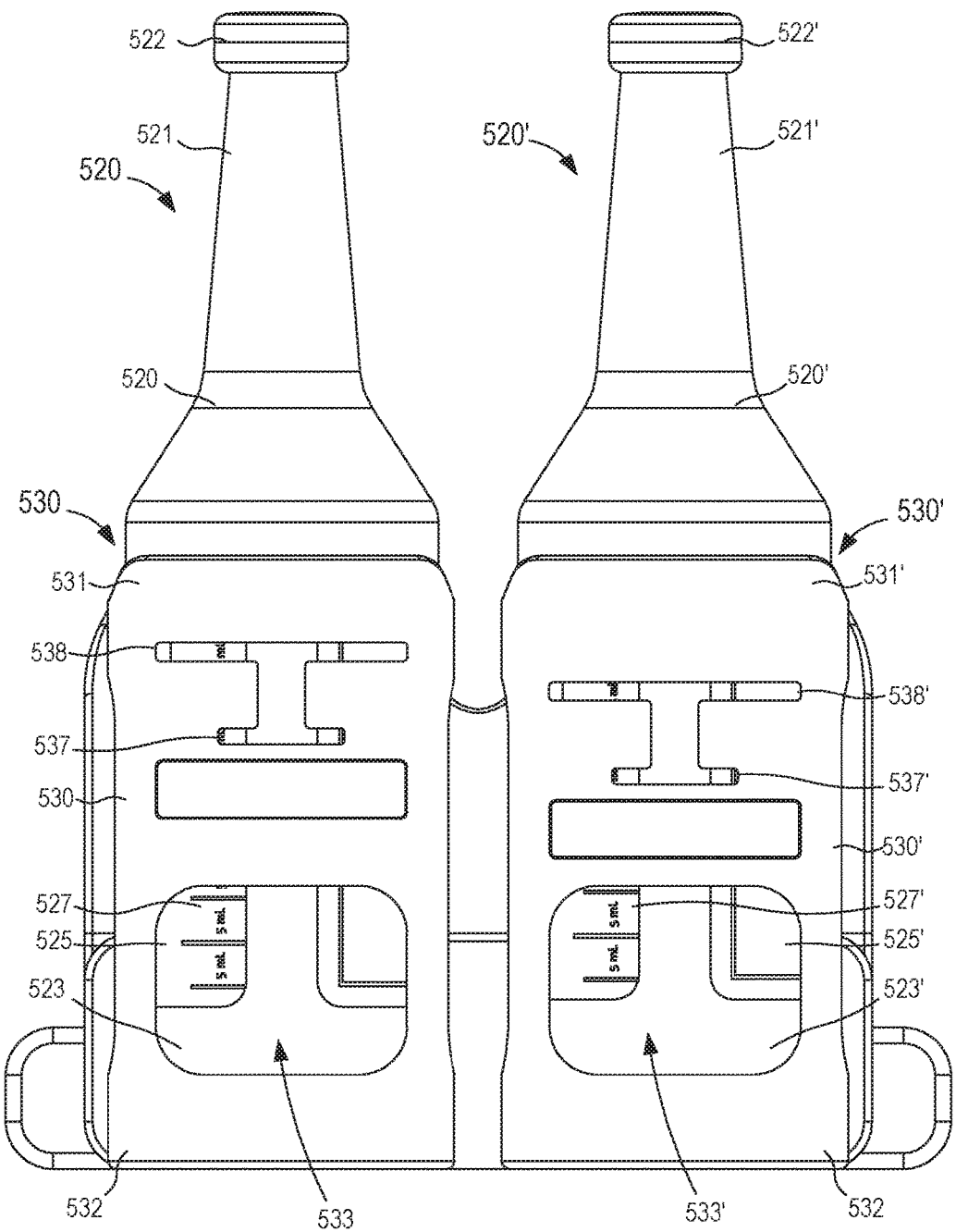
FIG. 7 is a side view of a cradle coupled to a first volumetric verification device and a second volumetric verification device, which in turn are disposed about a portion of a first sample reservoir and a second sample reservoir, respectively, according to an embodiment.

In some embodiments, a sample reservoir can be configured to engage and/or couple to a volumetric verification device (such as those described herein), which in turn is coupled to a cradle, mounting device, holder, and/or the like configured to facilitate the procurement of a sample. For example, FIGS. 7-10 illustrate a pair of volumetric verification devices 530 and 530' that can be coupled to a cradle 550 and that are configured to receive a portion of a sample reservoir 520 and 520', respectively. The sample reservoirs 520 and 520' can be any suitable sample reservoir such as any of those described herein. For example, as shown in FIG. 7, the sample reservoir 520 includes at least a proximal end portion 521, a distal end portion 522, and a label 525 having at least a volume indicator portion 527. Similarly, the sample reservoir 520' includes at least a proximal end portion 521', a distal end portion 522', and a label 525 having at least a volume indicator portion 527'. Moreover, the sample reservoir 520 can be substantially the same as the sample reservoir 520' (e.g., the sample reservoirs 520 and 520' can each include an aerobic culture medium or can each include an anaerobic culture medium). In this embodiment, however, the sample reservoir 520 includes, for example, an anaerobic culture medium, while the sample reservoir 520' includes, for example, an aerobic culture medium (or vice versa). In this manner, the sample reservoirs 520 and 520' can be substantially similar in form and function as the sample reservoir 220 described above with reference to FIGS. 2-4; thus, the sample reservoirs 520 and 520' are not described in further detail herein.

The verification devices 530 and 530' can be any suitable volumetric verification device such as those described herein. By way of example, the verification device 530 includes a proximal end portion 531 and a distal end portion 532, and defines an inner volume 533 configured to receive a portion of the sample reservoir 520. Furthermore, the verification device 530 defines a first opening 537, a second opening 538, a viewing window 539, and an identification window 540. Similarly, the verification device 530' includes a proximal end portion 531' and a distal end portion 532', and defines an inner volume 533' configured to receive a portion of the sample reservoir 520'. Furthermore, the verification device 530' defines a first opening 537', a second opening 538', a viewing window 539', and an identification window 540'. In some embodiments, the verification devices 530 and 530' can be substantially the same. For example, the verification devices 530 and 530' can each be configured to receive a sample reservoir of the same type (e.g., including an aerobic culture medium or an anaerobic culture medium). In this embodiment, however, the verification device 530 receives the sample reservoir 520 including, for example, the anaerobic culture medium (as described above), while the verification device 530' receives the sample reservoir 520' including, for example, the aerobic culture medium (or vice versa).

As shown in FIG. 7, the arrangement of the verification device 530 is such that when the sample reservoir 520 is disposed in the verification device 530, the first opening 537 is substantially aligned with a top surface of the culture medium disposed in the sample reservoir 520. In addition, the second opening 538 is spaced a distance from the first opening 537 to allow for visualization of a meniscus of a volume of bodily fluid when the volume is within a desired range or tolerance of volumes associated with that culture medium (e.g., about 8 mL to about 10 mL), as described in detail above with reference to the verification device 330 and sample reservoir 320 in FIG. 5. The first opening 537' and the second opening 538' of the verification device 530' are similarly arranged relative to the sample reservoir 520'. In this manner, the verification devices 530 and 530' can be substantially similar in form and function as the verification device 330 described in reference to FIG. 5; thus, aspects of the verification devices 530 and 530' that are similar to the corresponding aspects of the verification device 330 in FIG. 5 are not described in further detail herein.

Figure 8:
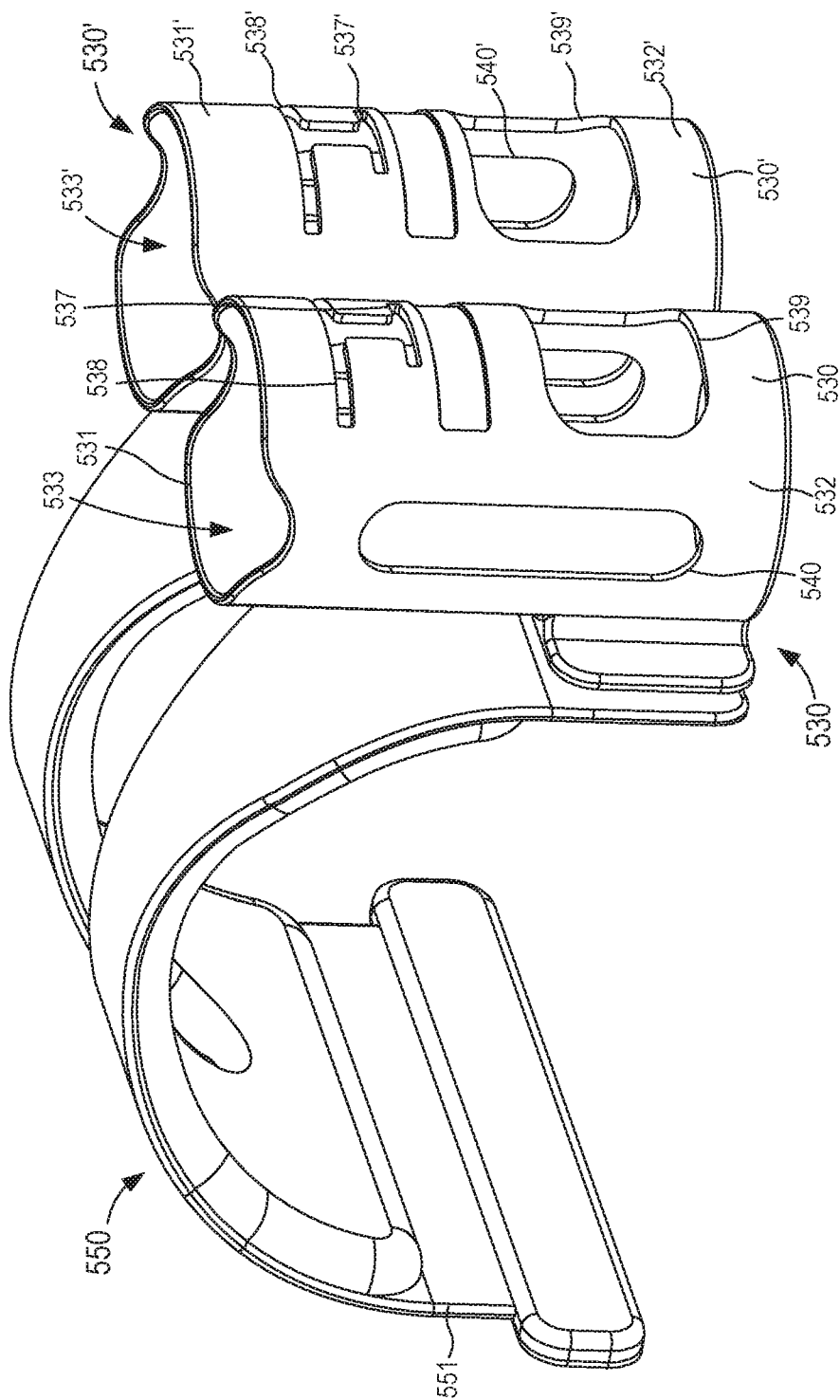
FIG. 8 is a perspective view of the cradle coupled to the first volumetric verification device and the second volumetric verification device of FIG. 7.
Figure 9:
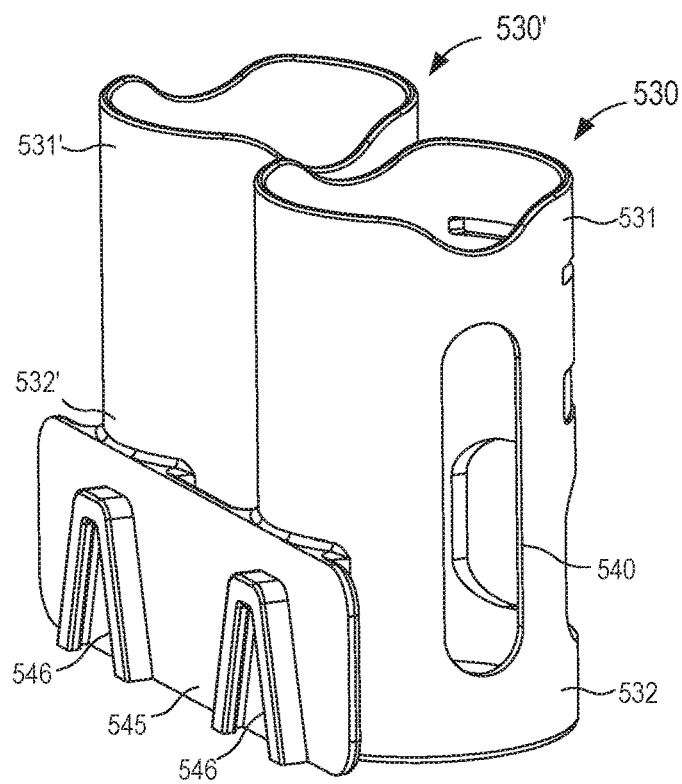
FIG. 9 is a rear perspective view of the first volumetric verification device and the second volumetric verification device of FIG. 7.

The verification devices 530 and 530' can differ from the verification device 330, however, by being configured to couple to the cradle 550. For example, as shown in FIGS. 8 and 9, the verification devices 530 and 530' are coupled to and/or otherwise include a coupling portion 545 having a set of coupling members 546. In some embodiments, the coupling portion 545 can be unitarily formed with the verification devices 530 and 530'. In other embodiments, the coupling portion 545 can be attached and/or otherwise coupled to the verification devices 530 and 530' via, for example, ultrasonic welding, an adhesive, an interference fit, a snap fit, a mechanical fastener (e.g., bolt, screw, rivet, etc.), and/or the like. The coupling members 546 can extend from a surface of the coupling portion (e.g., a surface opposite the surface in contact with the verification devices 530 and 530') to selectively engage a corresponding set of coupling members 553 on the cradle 550, as described in further detail herein. Although shown in FIG. 9 as including two coupling members 546, in other embodiments, the coupling portion 545 can include any suitable number of coupling members 546 such as, for example, one, three, four, five, or more.

Figure 10:
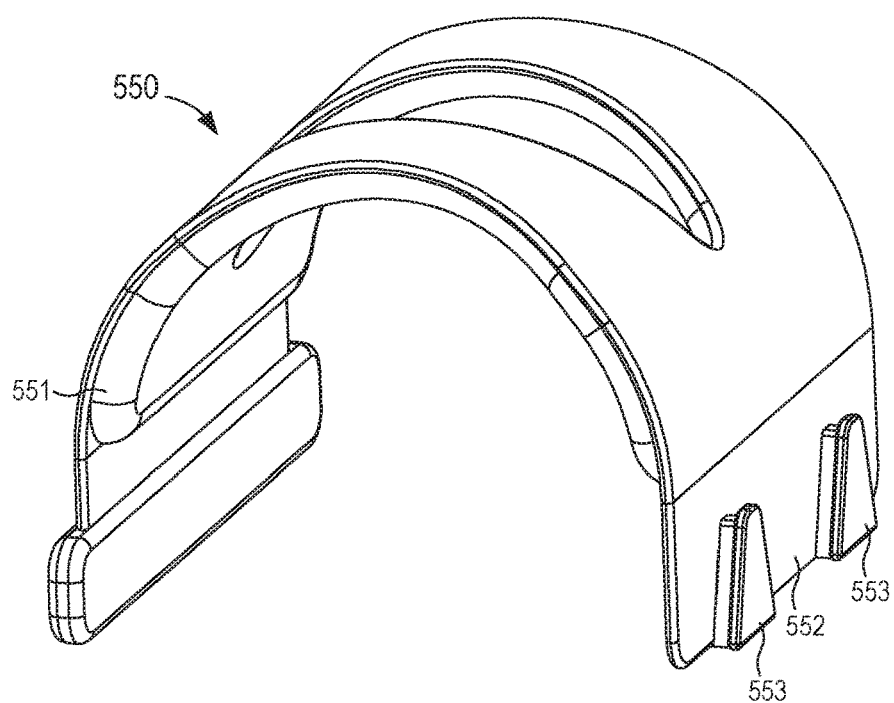
FIG. 10 is a front perspective view of the cradle of FIG. 7.

The cradle 550 includes a body portion 551 and a coupling portion 552. The body portion 551 can be any suitable shape, size, or configuration. For example, as shown in FIG. 10, the body portion 551 can have a cross-sectional shape that is substantially U-shaped. In some embodiments, the shape and/or size of the body portion 551 can be associated with a portion of the human body and/or a portion of an item about which the body portion 551 can be disposed. For example, in this embodiment, the body portion 551 has a shape and size associated with a portion of a human arm. In other words, the body portion 551 is configured to be disposed about a portion of a user's arm or a portion of a patient's arm. Said another way, a portion of a user's arm can be disposed within the substantially U-shaped body portion 551, thereby at least temporarily coupling the cradle 550 to the user's arm. In other embodiments, the body portion 551 can have a size and/or shape associated with, for example, a hospital bed rail, and or any other suitable structure (e.g., an inanimate structure). In some embodiments, the body portion 551 can be formed from a relatively resilient material and/or the like that can allow the body portion 551 to be bent, flexed, deformed, molded, and/or otherwise substantially conformed about a portion of the human body (e.g., an arm) or a portion of any other suitable object. Thus, the cradle 550 can be maintained in a relatively fixed position relative to the item or portion of the body about which the body portion 551 is disposed.

The coupling portion 552 of the cradle 550 includes the set of coupling members 553. As described above, the coupling members 553 are configured to engage and/or couple to the corresponding coupling members 546 of the coupling portion 545 to couple the verification devices 530 and 530' to the cradle 550. For example, as shown in FIG. 10, the coupling members 553 extend from a surface of the coupling portion 552 and each include a triangular and/or wedge-shaped flange. Accordingly, the coupling members 546 of the coupling portion 545 can have a size and shape associated with the coupling members 553 of the cradle 550. Thus, the coupling portion 545 can be manipulated to dispose the coupling members 546 of the coupling portion 545 about the coupling members 553 of cradle 550 to define, for example, a friction fit, an interference fit, a snap fit, and/or the like, which in turn, is operative in coupling the verification devices 530 and 530' to the cradle 550. In other embodiments, the coupling portion 545 attached and/or coupled to the verification devices 530 and 530' can be coupled to the coupling portion 552 of the cradle 550 in any suitable manner. Thus, in use, the sample reservoirs 520 and 520' can be disposed in the verification devices 530 and 530', which in turn, are coupled to the cradle 550. Thus, the cradle 550 can be positioned relative to and/or disposed about a portion of the human body and/or any other suitable object to limit movement of the sample reservoirs 520 and 520' when being filled with a bodily fluid and/or when a user is visualizing the contents of the sample reservoirs 520 and/or 520' via the first opening 537 and/or the second opening 538 of the verification device 530 and/or the first opening 537' and/or the second opening 538' of the verification device 530', respectively.

Figure 11:
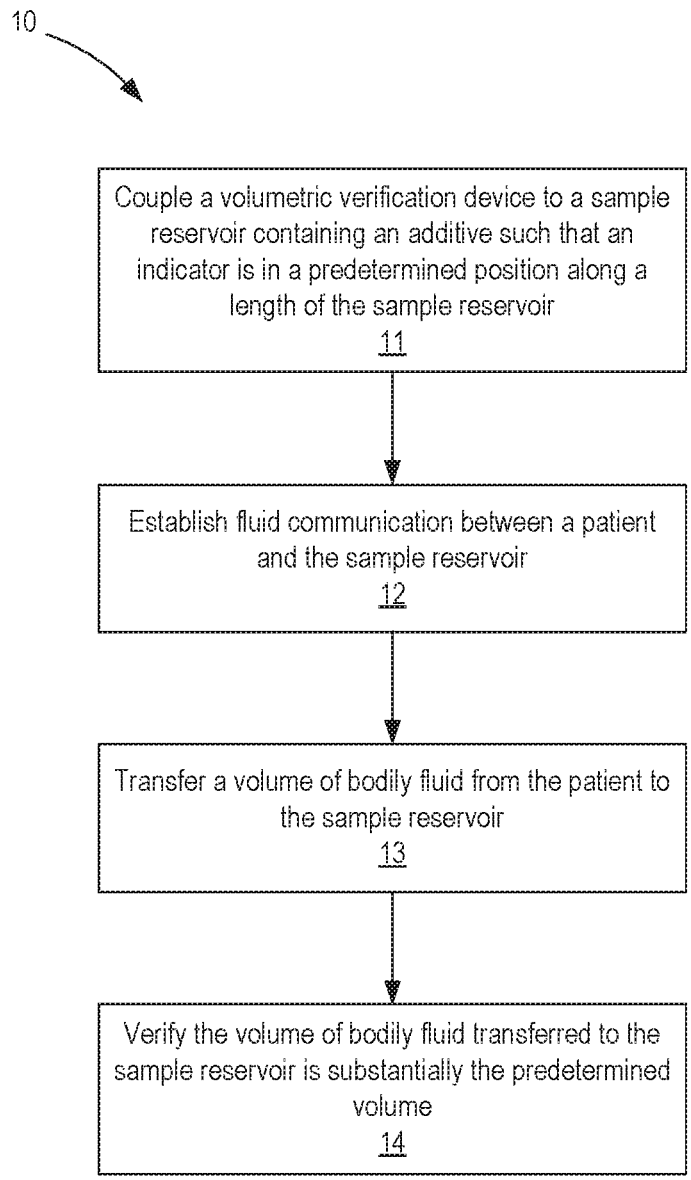
FIG. 11 is a flowchart illustrating a method of verifying a sample volume according to an embodiment.

FIG. 11 is a flowchart illustrating a method 10 of verifying a sample volume according to an embodiment. The method includes coupling a volumetric verification device to a sample reservoir containing an additive such that an indicator is in a predetermined position along a length of the sample reservoir, at 11. For example, as described above with reference to the verification device 230, a user can position the verification device about the sample reservoir to place the indicator in a desired position. The desired position can be, for example, associated with a desired fill volume and/or fill height of the sample reservoir. In some embodiments, the indicator can be a marker or the like configured to produce a mark on a portion of the sample reservoir such as a label (as described above with reference to the sample reservoir 220). In such embodiments, the user can exert a force on a portion of the verification device to place the indicator in contact with a portion of the sample reservoir and can rotate the verification device about the sample reservoir, which in turn, results in the indicator providing a visual indication on the sample reservoir associated with a desired fill volume. While the indicator is described as being a marker, in other embodiments, the indicator can be, for example, a window or the like defined by the verification device, as described above with reference to the verification device 330.

With the indicator in the predetermined position, fluid communication is established between a patient and the sample reservoir, at 12. For example, the sample reservoir can be placed in fluid communication with any suitable fluid transfer device such as those described herein. A volume of bodily fluid is transferred from the patient to the sample reservoir, at 13. In some embodiments, the volume of bodily fluid can be based on the additive (e.g., culture medium or the like) disposed in the sample reservoir. In some embodiments, the volume of bodily fluid can be between about 8 mL and about 10 mL. In other words, the desired fill volume of the sample reservoir can be between about 8 mL and about 10 mL corresponding to the additive disposed in the sample reservoir. For example, as described above, the additive can be a culture medium such as an aerobic culture medium, an anaerobic culture medium, and/or the like, each of which is associated with a predetermined fill volume of the sample reservoir.

The method 10, includes verifying the volume of bodily fluid transferred to the sample reservoir is substantially the predetermined volume of bodily fluid, at 14. For example, the user can transfer a bodily fluid into the sample reservoir (e.g., via any suitable transfer device described herein) and can stop the transfer of bodily fluid when a volume of the bodily fluid is substantially equal to the predetermined volume associated with the position of the indicator. More specifically, the user can stop the transfer of bodily fluid when a surface and/or meniscus of the bodily fluid within the sample reservoir is substantially aligned with the indicator. In this manner, a verification device corresponding to a given culture medium and/or additive can be used to verify a sample volume of bodily fluid is within, for example, an accepted tolerance and/or the like.

Although not shown in FIGS. 2-10, the sample reservoirs 220, 320, 420, 520, and 520' and the verification devices 230, 330, 430, 530, and 530' can be used with any suitable fluid transfer device such as, for example, those described above with reference to FIG. 1. For example, such a transfer device can be any substantially similar to and/or the same as any of those described in the '724 Patent and/or the '782 Publication, incorporated by reference above. Thus, in use, such a transfer device can be placed in fluid communication with the sample reservoirs 220, 320, 420, 520 and/or 520' and the transfer device can be placed in a configuration in which a first volume of bodily fluid and/or a pre-sample volume of bodily fluid is diverted into, for example, a pre-sample reservoir. In this manner, undesirable microbes such as, for example, dermally residing microbes dislodged during a venipuncture can be transferred into to the pre-sample reservoir.

Once predetermined volume of bodily fluid is disposed in the pre-sample reservoir, the pre-sample reservoir is fluidically isolated from the port to sequester the pre-sample volume of bodily fluid in the pre-sample reservoir. In some embodiments, the predetermined pre-sample volume can be about 0.1 mL, about 0.3 mL, about 0.5 mL, about 1.0 mL, about 2.0 mL, about 4.0 mL, about 4.0 mL, about 5.0 mL, about 10.0 mL, about 20 mL, about 50 mL, and/or any volume or fraction of a volume therebetween. In other embodiments, the pre-sample volume can be greater than 50 mL or less than 0.1 mL. In other embodiments, the predetermined pre-sample volume can be between about 2 mL and about 5 mL. In still other embodiments, the predetermined pre-sample volume can be about 4 mL. Thus, once the pre-sample reservoir is fluidically isolated, the transfer device can be manipulated to transfer, for example, a sample volume of bodily fluid into any of the sample reservoirs 220, 320, 420, 520, and/or 520'. Moreover, as the bodily fluid is transferred to the sample reservoir 220, 320, 420, 520, and/or 520', any of the verification devices 230, 330, 430, 530, and/or 530' can be used to verification and/or otherwise determine a sample volume within the sample reservoir 220, 320, 420, 520, and/or 520'. In some embodiments, the sample volume of bodily fluid can be any suitable volume of bodily fluid from, for example, one or a few drops of bodily fluid (e.g., nanoliters or microliters) to 10 mL, 20 ml, 30 mL, 40 mL, 50 mL, 100 mL, 1,000 mL, 10,000 mL, or more (or any value or fraction of a value therebetween) of bodily fluid. As such, the embodiments described herein can significantly reduce the occurrence of false-positives or false-negatives from post-collection analysis.

The embodiments described herein can be formed from any suitable material or combination of materials. For example, the embodiments described herein can be formed from a biocompatible plastic or the like, and such embodiments can be, for example, reusable. Alternatively, any of the embodiments described herein can be formed from a cardboard and/or paper product, and such embodiments can be, for example, disposable.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

Any of the embodiments and/or components of the embodiments can be packaged and sold independently or packaged and sold as a kit having any suitable combination of components. For example, in some embodiments, a kit can include any one of the sample reservoirs described herein and any one of the verification devices described herein. In some embodiments, a kit can include multiple sample reservoirs (e.g., two or more) and multiple verification devices (e.g., two or more). In some such embodiments, the sample reservoirs can be substantially the same and can contain, for example, substantially the same additive and/or culture medium. Accordingly, the verification devices can each be substantially the same and can correspond to and/or can be associated with the additive disposed in the sample reservoirs. In other embodiments, the sample reservoirs can have substantially the same size and/or shape but can contain different culture mediums, reagents, additives, amounts of negative pressure, and/or the like. As such, the kit can include at least one verification device configured for use with each sample reservoirs. In some such embodiments, the verification devices can each be the same and can be configured for use with, for example, aerobic or anaerobic culture mediums such as, for example, the verification device 220 described above. In other embodiments, the verification devices can be different and configured for use with one culture medium such as the verification device 330. While kits are described as including at least one sample reservoir and at least one verification device, in other embodiments, a kit can include multiple verification devices (two or more) without one or more sample devices (or vice versa). In such embodiments, a kit can be a multi-pack of the same verification devices or a multi-pack of the same sample reservoirs. In other embodiments, a kit can be a variety of verification devices or a variety of sample devices. In still other embodiments, a kit can include a cradle or the like such as the cradle 550 and/or can include any other coupling and/or retention device. In some embodiments, a kit can include one or more verification devices, one or more sample reservoirs, and any suitable fluid transfer or portion thereof.

The specific configurations of the various components can also be varied. For example, the size and specific shape of the various components can be different from the embodiments shown, while still providing the functions as described herein. More specifically, the size and shape of the various components can be specifically selected for a desired volume of bodily fluid or a desired rate of bodily fluid flow into a sample reservoir. For example, while the sample reservoirs are particularly shown and described herein, the verification devices described herein can be used with any suitable fluid reservoir. For example, in some embodiments, a sample reservoir can be substantially similar to or the same as known sample containers such as, for example, a Vacutainer® (manufactured by BD), a BacT/ALERT® SN or BacT/ALERT® FA (manufactured by Biomerieux, Inc.), a Nanotainer™ (manufactured by Theranos), and/or any suitable reservoir, vial, microvial, microliter vial, container, microcontainer, and/or the like. As such the size and/or configuration of the sample reservoir can be based on, for example, a volume of bodily fluid configured to be contained therein.

In some embodiments, a collection device can include a flow-metering device and/or any other mechanism, device, or method configured to measure volumetric flow rates and/or characteristics of a bodily fluid such as, for example, a pressure sensor, a voltage sensor, a photo sensor, a velocity sensor, a flow meter, a strain gauge, a valve, a turbine, a float, displacement analysis, density analysis, weight analysis, optical analysis, ultrasound analysis, thermal analysis, Doppler analysis, electromagnetic field (emf) analysis, reflection analysis, obstruction analysis, area analysis, venturi analysis, coriolis analysis, visual analysis, and/or any other suitable sensor, analysis, and/or calculation (e.g., applying and/or using, for example, Boyle's law, ideal gas law, force calculation (force=mass*acceleration), and/or the like). For example, any of the embodiments described herein can include a flow-metering device such as those described in the '782 Publication.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed:

1. A system for verifying a sample volume, comprising:
a sample reservoir defining an inner volume and configured to receive a volume of bodily fluid, the inner volume containing an additive;
a volumetric verification device including a first indicator and a second indicator, the volumetric verification device configured to selectively engage the sample reservoir to (1) place the first indicator in a first position along a length of the sample reservoir such that the first indicator is substantially aligned with a surface of the additive and (2) place the second indicator in a second position along the length of the sample reservoir such that the second indicator is substantially aligned with a predetermined fill volume when bodily fluid is transferred to the inner volume; and
a cradle configured to be coupled to the volumetric verification device, the cradle configured to support the volumetric verification device and the sample reservoir when bodily fluid is transferred to the inner volume.

2. The system of claim 1, wherein the sample reservoir is configured to receive the volume of bodily fluid such that the sum of the volume of bodily fluid and a volume of the additive substantially equal the predetermined fill volume.

3. The system of claim 1, wherein the first indicator is a first window defined by the volumetric verification device and the second indicator is a second window defined by the volumetric verification device.

4. The system of claim 1, wherein a position along the length of the sample reservoir is associated with a fill volume of the sample reservoir.

5. The system of claim 4, wherein the second position along the length of the sample reservoir is associated with the predetermined fill volume.

6. The system of claim 1, wherein the first position along the length of the sample reservoir is separated from the second position along the length of the sample reservoir by a distance, a portion of the inner volume between that distance being equal to a volume of the additive.

7. The system of claim 1, wherein the additive is at least one of an aerobic culture medium and an anaerobic culture medium.

8. The system of claim 1, wherein the predetermined fill volume is a first predetermined fill volume when the sample reservoir contains a first additive,
the predetermined fill volume is a second predetermined fill volume different from the first predetermined fill volume when the sample reservoir contains a second additive different from the first additive.

9. A kit for verifying a sample volume, comprising:
a volumetric verification device of claim 8, the volumetric verification device is a first volumetric verification device that is configured to engage the sample reservoir when the sample reservoir contains the first additive; and
a second volumetric verification device including a first indicator and a second indicator, the second volumetric verification device configured to selectively engage the sample reservoir when the sample reservoir contains the second additive such that the first indicator of the second volumetric verification device is substantially aligned with a surface of the second additive and the second indicator of the second verification device is substantially aligned with the second predetermined fill volume.

10. The kit of claim 9, further comprising:
a first sample reservoir, the first sample reservoir containing the first additive, the first volumetric verification device configured to selectively engage the first sample reservoir; and
a second sample reservoir, the second sample reservoir containing the second additive, the second volumetric verification device configured to selectively engage the second sample reservoir.

11. The kit of claim 9, wherein the cradle is a first cradle, the kit further comprising:
a second cradle configured to be coupled to the first volumetric verification device and the second volumetric verification device, the second cradle configured to support the first volumetric verification device and the second volumetric verification device.

12. A system for verifying a sample volume, comprising:
a sample reservoir defining an inner volume and configured to receive a volume of bodily fluid, the inner volume containing an additive, the sample reservoir including a label having a volumetric indicator portion configured to provide an indication of a fill volume within the sample reservoir; and
a volumetric verification device including a marker, the volumetric verification device configured to selectively engage the sample reservoir to place the marker in a predetermined position along the volumetric indicator portion of the sample reservoir, the predetermined position based on the additive contained in the inner volume.

13. The system of claim 12, wherein a portion of the sample reservoir has a predetermined color associated with the additive contained in the inner volume, a color of a portion of the volumetric verification device including the marker being the predetermined color.

14. The system of claim 12, wherein the sample reservoir has a length, a position along the length of the sample reservoir indicative of a fill volume.

15. The system of claim 14, wherein the volumetric indicator portion of the label is configured to provide an indication associated with a position along the length of the sample reservoir.

16. The system of claim 12, wherein the volumetric indicator portion includes indicia configured to indicate a fill volume of the sample reservoir.

17. The system of claim 12, wherein the volumetric indicator portion includes indicia configured to indicate a fill volume of the sample reservoir, the predetermined position along the volumetric indicator portion is a position along the indicia, and
the marker is configured to produce a mark at the position along the indicia indicative of a predetermined fill volume associated with the additive.

18. The system of claim 17, wherein the mark is at least one of a colored line, a score, a scrape, and an indentation at the predetermined position along the volumetric indicator portion.

19. The system of claim 12, wherein the additive is one of an aerobic culture medium and an anaerobic culture medium.

20. The system of claim 19, wherein the marker is a first marker and the predetermined position is a first predetermined position, the first marker is configured to produce a mark at the first predetermined position along the volumetric indicator portion that is substantially aligned with a first predetermined fill volume when the sample reservoir contains the aerobic culture medium, and the volumetric verification device includes a second marker configured to be placed in a second predetermined position different from the first predetermined position along the volumetric indicator portion of the sample reservoir, the second marker is configured to produce a mark at the second predetermined position along the volumetric indicator portion that is substantially aligned with a second predetermined fill volume when the sample reservoir contains the anaerobic culture medium.

* * * * *